(12) United States Patent
Hunter

(10) Patent No.: US 10,295,510 B1
(45) Date of Patent: May 21, 2019

(54) PART EVALUATION BASED UPON SYSTEM NATURAL FREQUENCY

(71) Applicant: VIBRANT CORPORATION, Albuquerque, NM (US)

(72) Inventor: Lemna J. Hunter, Corrales, NM (US)

(73) Assignee: Vibrant Corporation, Albuquerque, NM (US)

(*) Notice: Subject to any disclaimer, the term of this patent is extended or adjusted under 35 U.S.C. 154(b) by 590 days.

(21) Appl. No.: 14/831,766

(22) Filed: Aug. 20, 2015

Related U.S. Application Data

(60) Provisional application No. 62/039,728, filed on Aug. 20, 2014.

(51) Int. Cl.
*G01N 29/12* (2006.01)
*G01N 29/44* (2006.01)
*G06F 17/50* (2006.01)

(52) U.S. Cl.
CPC ......... *G01N 29/4445* (2013.01); *G01N 29/12* (2013.01); *G01N 29/4472* (2013.01); *G06F 17/5009* (2013.01); *G01N 2291/014* (2013.01); *G01N 2291/0258* (2013.01)

(58) Field of Classification Search
CPC ............ G06F 1/20; F01D 21/003; F01D 5/10; E21B 7/00; E21B 7/24; G05B 19/4185; H04L 67/12; F16F 15/18; H02K 33/16; H04R 17/005; G05D 1/00
USPC .............................................. 703/6
See application file for complete search history.

(56) References Cited

U.S. PATENT DOCUMENTS

| 7,140,252 B2 | 11/2006 | Hamidieh | |
|---|---|---|---|
| 8,167,826 B2* | 5/2012 | Oohashi | A61M 21/02 601/2 |
| 2011/0056750 A1* | 3/2011 | Lucon | E21B 7/24 175/56 |
| 2011/0077924 A1* | 3/2011 | Ertas | E21B 7/00 703/2 |
| 2012/0133308 A1* | 5/2012 | Elenga | H02P 25/032 318/128 |
| 2013/0079933 A1* | 3/2013 | Tan | G06F 1/20 700/280 |
| 2014/0030092 A1* | 1/2014 | Heinig | F01D 21/003 416/1 |

* cited by examiner

*Primary Examiner* — Kandasamy Thangavelu

(57) ABSTRACT

A part evaluation tool is disclosed and which may be used to assess a part-under-test for use in a system. A plurality of natural frequencies for a system operated at a first steady-state operational are identified. A vibrational response of a part-under-test is acquired, and resonance frequencies within this vibrational response are identified. Resonance frequencies of the part-under-test are compared with the identified natural frequencies for purposes of classifying the part as compliant (e.g., suitable for use in the system) or non-compliant (e.g., not suitable for use in the system).

27 Claims, 19 Drawing Sheets

PART EVALUATION BASED UPON SYSTEM NATURAL FREQUENCY

CROSS-REFERENCE TO RELATED APPLICATIONS

This patent application is a non-provisional patent application of and claims priority to U.S. Provisional Patent Application Ser. No. 62/039,728, entitled "PART EVALUATION BASED UPON SYSTEM NATURAL FREQUENCY," filed on Aug. 20, 2014, and the entire disclosure of which is incorporated by reference.

FIELD OF THE INVENTION

The present invention generally relates to the evaluation of a part and, more particularly, to evaluating a part that is used by a system that is operated at one or more steady-state operational frequencies.

BACKGROUND

A variety of techniques have been developed in which parts may be tested "nondestructively," meaning that the testing methodology enables defects to be identified without causing damage to the part. Examples of such nondestructive-testing methodologies include acoustic techniques, magnetic-particle techniques, liquid-penetrant techniques, radiographic techniques, eddy-current testing, and low-coherence interferometry, among others. There are various known advantages and disadvantages to each of these categories of testing methodologies, which are accordingly used in different environments.

Nondestructive-testing methods that use acoustic radiation generally operate in the ultrasonic range of the acoustic spectrum, and are valuable for a number of reasons. Such techniques are sensitive, for example, to both surface and subsurface discontinuities, enabling identification of defects both within the bulk and near the surface of a part. The depth of penetration for defect detection is generally superior to many other nondestructive-testing methodologies, and the techniques are highly accurate not only in determining the position of a defect, but also in estimating its size and shape.

SUMMARY

A first aspect of the present invention is directed to the evaluation of a part. A plurality of natural frequencies associated with a system are identified, where these natural frequencies are generated by or exist during operation of the system at a first steady-state operational frequency (which hereafter may be referred to as "selected natural frequencies"), and where the system includes a first part. A first vibrational response of a part-under-test (e.g., a candidate for use as the first part in the system) is acquired using at least one sensor, and a plurality of resonance frequencies of the part-under-test are identified in this first vibrational response (which hereafter may be referred to as "selected resonance frequencies"). The selected resonance frequencies of the part-under-test are compared with the selected natural frequencies of the system, and the part-under-test is classified based upon this comparison.

A number of feature refinements and additional features are applicable to the first aspect of the present invention. These feature refinements and additional features may be used individually or in any combination. The following discussion is applicable to at least the first aspect, up to the start of the discussion of a second aspect of the present invention.

At least one natural frequency that is compared to one or more resonance frequencies of the part-under-test, in accordance with the first aspect: 1) may be a natural frequency of an entirety of the system; 2) may be a natural frequency of a sub-system of the system; and/or 3) may be a natural frequency of an individual component of the system. Any appropriate number of natural frequencies may be identified and that are associated with operation of the system at the first steady-state operational frequency, including two or more natural frequencies. The multiple natural frequencies that are identified in association with operation of the system at the first steady-state operational frequency may be acquired in any appropriate manner, such as by modeling operation of the system at the first steady-state operational frequency (e.g., using a third aspect of the present invention, addressed below, to update a computer model of the system), such as by functional testing of the system (e.g., via operation of a prototype of the system at the first steady-state operational frequency), or both.

The comparison of the selected resonance frequencies of the part-under-test with the selected natural frequencies of the system may entail establishing/setting a separate natural frequency threshold for each selected natural frequency that is to be compared with the selected resonance frequencies of the part-under-test. Each natural frequency threshold may define a frequency range of any appropriate magnitude. One embodiment has each natural frequency threshold being set or established based upon information provided by an original equipment manufacturer. In any case, each natural frequency threshold that is utilized for the resonance frequency comparison may be acquired from any appropriate data source, such as by modeling operation of the system at the first steady-state operational frequency (e.g., using a third aspect of the present invention, addressed below, to update a computer model of the system), such as by functional testing of the system (e.g., via operation of a prototype of the system at the first steady-state operational frequency), or both.

The part-under-test may be of any appropriate type, for instance a new production part, an in-service part, an original equipment manufacturer or OEM part, a parts manufacturer approval or PMA part, or one that is a candidate for approval as a PMA part. Moreover, the part-under-test may be one that is being evaluated for use as the first part in the system. This first part may be one that moves at least at some point in time during the operation of the system at the first steady-state operational frequency, may be one that is stationary at least at some point in time during the operation of the system at the first steady-state operational frequency, or both. One embodiment has the first part moving throughout operation of the system at the first steady-state operational frequency. Another embodiment has the first part remaining stationary (at least relative to a remainder of the system) throughout operation of the system at the first steady-state operational frequency.

A separate natural frequency threshold may be associated with each selected natural frequency for the system and that is then compared with the selected resonance frequencies of the part-under-test in accordance with the first aspect. The comparison may entail comparing each selected resonance frequency of the part-under-test with the natural frequency threshold for each selected natural frequency of the system. If each selected resonance frequency of the part-under-testis outside of the natural frequency threshold for each selected natural frequency of the system, the part-under-test may be classified as a "compliant part." Otherwise, the part-under-test may be classified as a "non-compliant part."

A vibrational response of the part-under-test may be acquired at one or more times for comparison of the selected resonance frequencies of the part-under-test with the selected natural frequencies of the system. For instance, the method in accordance with the first aspect may be conducted on a part-under-test before the part is ever put into service into the system (i.e., a new production part), after the part has already been in incorporated by the system for any appropriate amount of time and during which the system was operated at least at the first steady-state operational frequency (i.e., an in service part), or both. The first aspect may be utilized in relation to acquisition of the vibrational response of the part-under-test at each of these times. All features of the first aspect relating to the first vibrational response and the part-under-test are applicable to each vibrational response that may be acquired on the part-under-test for comparison with the selected natural frequencies of the system.

Each vibrational response of the part-under-test may be acquired in any appropriate manner. At least one vibrational response of the part-under-test, more specifically its selected resonance frequencies, is compared with the selected natural frequencies of the system, all for purposes of classifying the part-under-test. The first vibrational response of the part-under-test may also be used for other purposes. For instance, the resonance frequencies in the first vibrational response of the part-under-test may be compared with a computer model of the first part for the system, and this comparison may be used to update the computer model of the first part (for instance, where this computer model of the first part is used as the data source for one or more other "tests" that may be conducted on the part-under-test, as discussed below).

One embodiment has the first vibrational response of the part-under-test being acquired through execution of a resonance inspection of the part-under-test. Features of such a resonance inspection are addressed in more detail below. Although it may be possible for a resonance inspection to be conducted on a part when incorporated by the system (e.g., an in situ resonance inspection of the part), it may be beneficial for the resonance inspection to be conducted on the part after it has been removed from the system (e.g., at a time when the part is disassociated from the system).

The comparison of the selected resonance frequencies in the first vibrational response of the part-under-test, with the selected natural frequencies of the system, may be characterized as one "test" for purposes of the first aspect. The first vibrational response of the part-under-test may be used in conjunction with at least one other "test," although each of the following tests may be used independently of the first aspect as well.

The first vibrational response of the part-under-test may be tested against a sort (e.g., a resonance inspection that utilizes such a sort). A "sort" may be characterized as an algorithm or a combination of algorithms that is used to determine if frequency-based criteria (i.e., one or more frequency-based criterion) exist in the frequency response of the part-under-test. Such a sort may be based upon data from a resonance inspection that was previously conducted on one or more parts, may be based upon computer modeling (e.g., as addressed in the third aspect in relation to an updated computer model for a part), may be based upon functional testing, or any combination thereof. This sort may be configured for the assessment of new production parts, may be configured for the assessment of in-service parts (or any other part for that matter), or may be configured to determine if a particular part is aging normally or abnormally.

The classification of the part-under-test may be based upon both the comparison of the selected resonance frequencies of the part-under-test with the selected natural frequencies of the system, along with the testing of the first vibrational response against a sort in accordance with the foregoing. For instance, the part-under-test may be characterized as a "compliant part" if both: 1) each resonance frequency of the selected resonance frequencies of the part-under-test is outside of a separate natural frequency threshold for each of the selected natural frequencies of the system; and 2) the execution of the sort on the first vibrational response yields a sort result in the form of a "compliant part classification" (e.g., the first vibrational response of the part-under-test passes the sort and where the sort is configured to identify one or more predetermined characteristics/attributes of a compliant part; the first vibrational response fails the sort and where the sort is configured to identify one or more predetermined characteristics/attributes of a non-compliant part). Conversely, a part-under-test may be characterized as a "non-compliant part" if one or more of the following exits: 1) at least one resonance frequency of the selected resonance frequencies of the part-under-test is within the natural frequency threshold of at least one of the selected natural frequencies of the system; or 2) the execution of the sort on the first vibrational response yields a sort result in the form of a "non-compliant part classification" (e.g., the first vibrational response passes the sort and where the sort is configured to identify one or more predetermined characteristics/attributes of a non-compliant part; the first vibrational response fails the sort and where the sort is configured to identify one or more predetermined characteristics/attributes of a compliant part).

Another test that may use the first vibrational response of the part-under-test includes comparing the first vibrational response to at least one resonance standard. Such a resonance standard may be based upon data from a resonance inspection that was previously conducted on one or more parts, or may be based upon computer modeling (e.g., as addressed in the third aspect in relation to an updated computer model for a part). This comparison with one or more resonance standards may be used in the assessment of both new production parts and in-service parts (or any other part for that matter), and furthermore may be used to determine if a particular part is aging normally or abnormally.

The classification of the part-under-test may be based upon both the comparison of the selected resonance frequencies of the part-under-test with the selected natural frequencies of the system, along with the comparison of the first vibrational response to at least one resonance standard. For instance, the part-under-test may be characterized as a "compliant part" if both: 1) each selected resonance frequency of the part-under-test is outside of a separate natural frequency threshold for each of the selected natural frequencies of the system; and 2) the first vibrational response of the part-under-test complies with at least one resonance standard that is associated with a compliant part (and/or if the first vibrational response of the part-under-test fails to comply with any resonance standard that is associated with a non-compliant part). Conversely, a part-under-test may be characterized as a "non-compliant part" if one or more of the following exits: 1) at least one of the selected resonance frequencies of the part-under-test is within the natural frequency threshold of at least one of the selected natural frequencies of the system; or 2) the first vibrational response of the part-under-test fails to comply with at least one resonance standard that is associated with a compliant part (and/or if the first vibrational response of the part-under-test complies with at least one resonance standard that is associated with a non-compliant part).

Yet another test that may use the first vibrational response of the part-under-test includes comparing each selected resonance frequency of the part-under-test to one or more resonance frequency thresholds, including where each resonance frequency threshold may be in the form of a certain frequency range. A "compliant part" may be one that has a separate resonance frequency in the first vibrational response for each specified resonance frequency threshold (e.g., where there is a separate resonance frequency from the first vibrational response within a different frequency range associated with each resonance frequency threshold). The classification of the part-under-test may be based upon both the comparison of the selected resonance frequencies of the part-under-test with the selected natural frequencies of the system, as well as the comparison of resonance frequencies of the part-under-test with the resonance frequency thresholds that are required for a compliant part classification. For instance, the part-under-test may be characterized as a "compliant part" if both: 1) each selected resonance frequency of the part-under-test is outside of a separate natural frequency threshold for each of the selected natural frequencies of the system; and 2) the first vibrational response includes a separate resonance frequency that complies with each resonance frequency threshold that is specified for a compliant part classification (e.g., there is a separate resonance frequency from the first vibrational response within the frequency range associated with each resonance frequency threshold that has been specified). Conversely, a part-under-test may be characterized as a "non-compliant part" if one or more of the following exits: 1) at least one selected resonance frequency of the part-under-test is within the natural frequency threshold of at least one of the selected natural frequencies of the system; or 2) at least one resonance frequency threshold that is required for a compliant part classification is not satisfied by any resonance frequency in the first vibrational response (e.g., the first vibrational response does not include a resonance frequency within the frequency range associated with at least one of the resonance frequency thresholds that has been specified).

Each resonance frequency threshold or range that is utilized by the first aspect may be determined/established in any appropriate manner. For instance, one or more resonance frequency ranges for use by the first aspect: 1) may be identified or otherwise selected from the resonance inspections results of a plurality of parts; 2) may be identified or otherwise selected from a computer model of the first part (e.g., as addressed in the third aspect in relation to an updated computer model for a part); or 3) from functional testing of one or more parts.

The part-under-test may also be tested to determine if the part-under-test resonates at least substantially the same as at least one compliant part. A part-under-test may be classified as a "compliant part" if it resonates at least substantially the same as least one other part that has previously been determined to be a compliant part. The classification of the part-under-test may be based upon both the comparison of the selected resonance frequencies of the part-under-test with the selected natural frequencies of the system, along with the noted resonation comparison. For instance, the part-under-test may be characterized as a "compliant part" if both: 1) each of the selected resonance frequencies of the part-under-test is outside of a separate natural frequency threshold for each of the selected natural frequencies of the system; and 2) the part-under-test resonates at least substantially the same as at least one other compliant part. Conversely, a part-under-test may be characterized as a "non-compliant part" if one or more of the following exits: 1) at least one selected resonance frequency of the part-under-test is within the natural frequency threshold of at least one of the selected natural frequencies of the system; or 2) the part-under-test fails to resonate at least substantially the same as at least one other compliant part.

A number of implementations are envisioned in relation to the first aspect. One is that an original equipment manufacturer may specify the requirements associated with the classification of the part-under-test (e.g., to establish a compliant part classification or the like), and the part-under-test may be from a non-OEM entity (e.g., the first aspect may be configured for the assessment of non-OEM parts). The first aspect may be implemented to assess multiple designs of the same part, where each of these designs may be encompassed by a common product specifications standard. In certain cases, a product specifications for the first part of the system may be updated from time to time. The first aspect may be used to assess a first part-under-test that is in accordance with a first product specifications standard for the first part of the system, and furthermore may be used to assess a second part-under-test that is in accordance with a second product specifications standard for the first part of the system, where the second product specifications standard is an update of the first product specifications standard. The first aspect may be used to determine if an update of a product specifications standard for the first part is appropriate.

There may be situations where the first part for the system is completely redesigned. The first aspect may be used to assess the redesign, for instance to determine if the redesign of the first part is still suitable for implementation into the system. Of course the first aspect may be used to assess an original design of a part for the system as well. The first part for the system may be repaired or refurbished. The first aspect may be used to determine that the first part is still suitable for incorporation back into the system after having been repaired or refurbished.

The first aspect is also applicable to assessing the manufacture of parts for use as a first part in the system. It is possible that different manufacturing protocols may be used to manufacture the same part for use as the first part in the system. A first part-under-test may be manufactured according to a first manufacturing protocol that is within a manufacturing specifications standard for the first part, while a second part-under-test may be manufactured according to a second manufacturing protocol. This second manufacturing protocol may be different from the first manufacturing protocol, but the second manufacturing protocol may still be within the manufacturing specifications standard for the first part. The first aspect may be used to assess parts that are manufactured in accordance with the first manufacturing protocol, and also may be used to assess parts that are manufactured in accordance with the second manufacturing protocol. The first aspect may also be utilized to validate a manufacturing process for parts to be used as a first part in the system (e.g., to confirm that parts that are manufactured in accordance with such a manufacturing process are suitable for use in the system), whether in the form of an original manufacturing process/protocol or a revised/modified/updated manufacturing process/protocol.

A second aspect of the present invention is directed to the evaluation of a part. A first resonance inspection is conducted on a first part, where a first frequency response of the first part is acquired by exciting the first part at a plurality of input frequencies. The first frequency response of the first part is tested against a sort. This sort is based upon resonance inspection results of at least one part, where this part has passed operational certification testing for purposes of validating a design of the part. The first part is assigned to a compliant part classification if the sort provides a compliant part classification sort result. In order for the first part to be assigned a compliant part classification, the first frequency response of the first part must include a first resonance frequency that is within a first frequency range. That is, the sort is configured to require a first resonance frequency that is within a first frequency range in order for the sort to yield a compliant part classification sort result.

A number of feature refinements and additional features are applicable to the second aspect of the present invention. These feature refinements and additional features may be used individually or in any combination. The following discussion is applicable to at least the second aspect, up to the start of the discussion of a third aspect of the present invention. Initially, this second aspect may be used in combination with the above-noted first aspect.

The first part may be assigned to a non-compliant part classification if the sort provides a non-compliant part classification sort result. A non-compliant part classification sort result may be generated by the sort if the first frequency response of the first part lacks or fails to include a resonance frequency within the first frequency range.

One embodiment has the sort being used to evaluate parts only after a determination has been made that the part actually passed the operational certification testing. So long as the part has in fact passed operational certification testing, the resonance inspection results that are used to define the sort for the second aspect may be based upon: 1) a resonance inspection of such a part after having completed the operational certification testing but before this part has actually been put into service; or 2) a resonance inspection of such a part after having completed the operational certification testing, and furthermore after this part has actually been put into service for a certain period of time (e.g., an in-service part that has itself also previously passed operational certification testing).

The sort may be configured to also require a separate resonance frequency within each of a plurality of different frequency ranges, including where none of these different frequency ranges overlap to any extent. For instance, the sort may be configured to require a second resonance frequency within a second frequency range. One embodiment has the first frequency range being completely separate from the second frequency range, or where there is no overlap between the first frequency range and the second frequency range (e.g., the first and second frequency ranges may be selected such that there is not a single frequency that exists in both the first frequency range and the second frequency range). In any case, in order for the first part to be assigned a compliant part classification in this example, the first frequency response of the first part must include a first resonance frequency that is within the first frequency range, and the first frequency response of the first part must include a second resonance frequency that is within the second frequency range. That is, the sort may be configured to require a first resonance frequency that is within a first frequency range and to require a second resonance frequency that is within a second frequency range, all in order for the sort to yield a compliant part classification sort result. Conversely, a non-compliant part classification sort result may be generated by the sort if one or more of the following exits: 1) the first frequency response of the first part lacks or fails to include a first resonance frequency within the first frequency range; 2) if the first frequency response of the first part lacks or fails to include a second resonance frequency within the second frequency range; or 3) the first frequency response of the first part lacks or fails to include a first resonance frequency within the first frequency range, and the first frequency response of the first part also lacks or fails to include a second resonance frequency within the second frequency range.

A third aspect of the present invention pertains to modeling, for instance for purposes of identifying one or more natural frequencies of a system for use in conjunction with the above-noted first aspect. A frequency response of a part-under-test is acquired. A first transfer function is applied to this first frequency response to define a second frequency response (or a first transformed frequency response). This second frequency response is associated with the part-under-test being vibrated in "free space." That is, the first transfer function transforms or translates the frequency response of the part-under-test (where the part-under-test may be in contact with one or more structures) for when the part-under-test is in free space (e.g., to predict how the part-under-test would respond, on a vibrational basis, when in free space). The second frequency response of the part-under-test is then compared to a modeled frequency response from a computer model of a part (e.g., associated with the part-under-test), and the computer model of the part is then updated accordingly (e.g., so that the computer model of the part more closely approximates the part-under-test at least on a vibrational or frequency response basis), and which may be referred to as an updated computer model of the part. A second transfer function is then applied to a modeled frequency response of the updated computer model of the part to define a third frequency response (or a second transformed frequency response). This third frequency response is associated with the part-under-test as it would vibrate when installed in a system and operated at a first steady-state operational frequency. That is, the second transfer function transforms or translates the frequency response of the part-under-test for the case where the part-under-test has now been installed back in the system (where the part-under-test may be in contact with one or more structures of the system). This may then be used to update a computer model for the system.

A number of feature refinements and additional features are applicable to the third aspect of the present invention. These feature refinements and additional features may be used individually or in any combination. The following discussion is applicable to at least the third aspect. Initially, this third aspect may be used in combination with the above-noted first aspect, alone or where the second aspect has also been implemented in conjunction with the first aspect.

The updated computer model of the part (corresponding with the part-under-test) may be used for any appropriate purpose, including as a data source for a resonance inspection. For instance, a sort may be based upon this updated computer model of the part, or a resonance standard may be based upon this updated computer model of the part. The updated computer model of the system also may be used for any appropriate purpose. For instance, the updated computer model of the system may be used to identify a plurality of natural frequencies of the system when the system is operated at a first steady-state operational frequency, such as for use in conjunction with the first aspect. The updated computer model of the system could also be used to establish or select a natural frequency threshold for each of a plurality of these natural frequencies of the system, such as for use in conjunction with the first aspect.

The various aspects of the present invention each may be implemented as a method and/or as an evaluation system or tool. Vibrational response data for use by the present invention may be acquired using a resonance inspection tool (although the resonance inspection tool is not required to actually perform a resonance inspection for purposes of the present invention). The vibrational data on a part being assessed for purposes of the present invention may be generated by exciting the part at a plurality of input frequencies and obtaining a frequency response of the part (e.g., to acquire/assess resonance data). This may be characterized as obtaining a whole body frequency response of the part using a number of different drive or input frequencies.

Data acquisition for purposes of the present invention may utilize a first transducer that excites or drives a part at multiple frequencies (e.g., by sweeping through a predetermined range of frequencies in any appropriate manner), along with at least one other transducer that measures the frequency response of this part to such excitations or drive frequencies (e.g., thereby encompassing using two or more "receiver" transducers). Any number of frequencies may be used to excite the part, and the excitation frequencies may be input to the part in any appropriate pattern and for any appropriate duration. Another option is to use a single transducer for acquiring vibrational data on the part. In this case, a transducer may drive the part at a certain frequency for a certain amount of time, and thereafter this same transducer may be used to obtain the frequency response of the part (e.g., after terminating the driving of the transducer at an input frequency). This may be repeated for multiple input or drive frequencies.

Any appropriate combination of excitation or drive frequencies may be used for vibrational data acquisition for use in conjunction with the present invention. Each transducer that is used to perform an inspection may be of any appropriate size, shape, configuration, and/or type. Although vibrational data acquisition could possibly be performed in situ (e.g., with the part in an installed condition or state), vibrational data acquisition will more typically be undertaken prior to installing a part for its end-use application or with the part being in an uninstalled condition or state.

Vibrational data acquisition in conjunction with the present invention may entail exciting a part-under-test using at least one drive transducer that is in contact with the part. Another option is to excite a part-under-test using at least one drive transducer that is maintained in spaced relation to the part-under-test throughout the acquisition of vibrational data. In one embodiment, such a drive transducer (e.g., a drive transducer that is spaced from the part-under-test for the inspection) may be in the form of a laser.

Any feature of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a resonance inspection system/tool utilizes "a frequency response transducer" alone does not mean that the resonance inspection system/tool utilizes only a single frequency response transducer). Moreover, any failure to use phrases such as "at least one" also does not limit the corresponding feature to the singular (e.g., indicating that a resonance inspection system/tool utilizes "a frequency response transducer" alone does not mean that the resonance inspection system/tool utilizes only a single frequency response transducer). Use of the phrase "at least generally" or the like in relation to a particular feature encompasses the corresponding characteristic and insubstantial variations thereof (e.g., indicating that a structure is at least generally cylindrical encompasses the structure being cylindrical). Finally, a reference of a feature in conjunction with the phrase "in one embodiment" does not limit the use of the feature to a single embodiment.

DETAILED DESCRIPTION

Various applications of resonance inspection (e.g., resonance ultrasound spectroscopy; process compensated resonance testing) are addressed herein. Various principles that may relate to resonance inspection are addressed in the following U.S. patents, the entire disclosures of which are incorporated by reference in their entirety herein: U.S. Pat. Nos. 5,408,880; 5,425,272; 5,495,763; 5,631,423; 5,641,905; 5,837,896; 5,866,263; 5,952,576; 5,965,817; 5,992,234; and 6,199,431.

Figure 1:
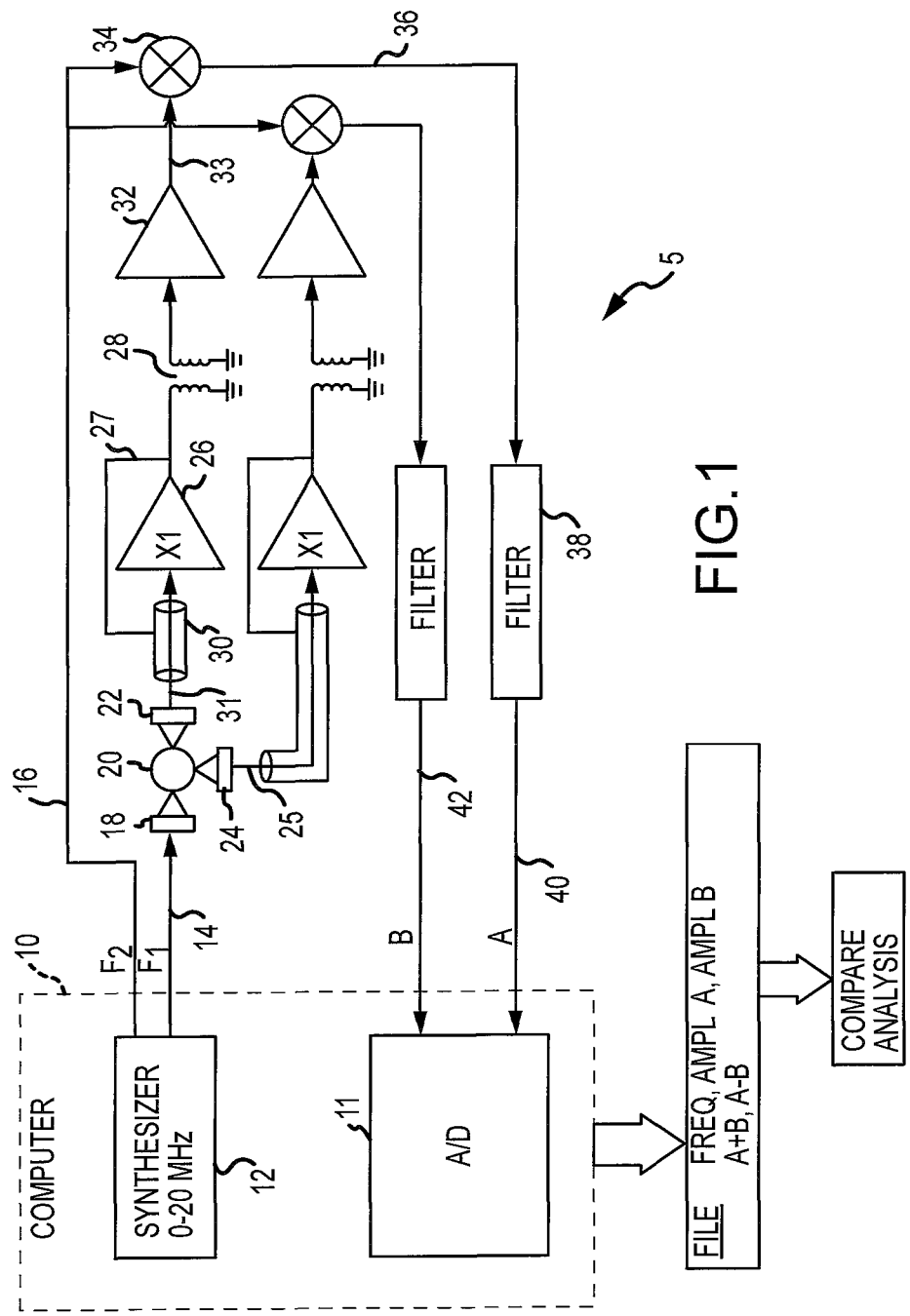
FIG. 1 is a block-diagram of one embodiment of a resonance inspection tool.
Figure 2:
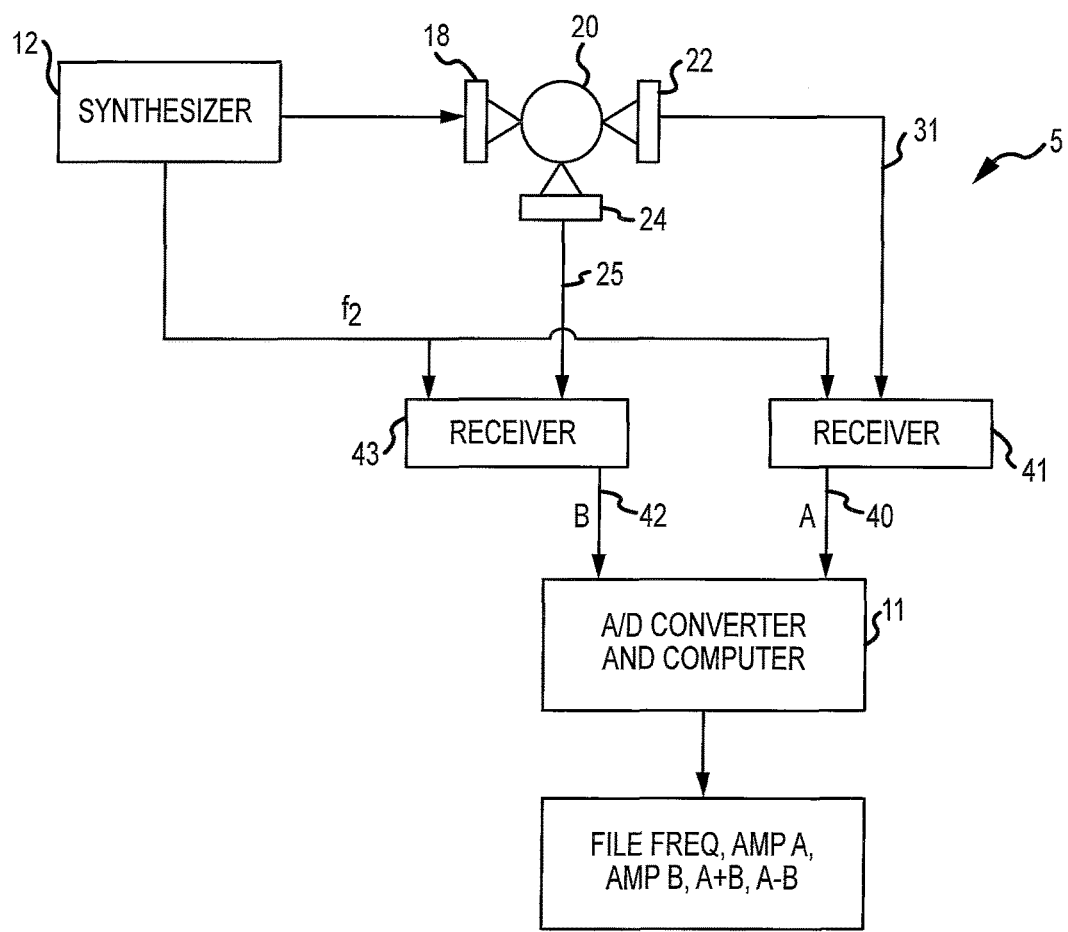
FIG. 2 shows a simplified block diagram of the resonance inspection tool of FIG. 1.

One embodiment of a resonance inspection tool or system (e.g., for accommodating resonant ultrasound spectroscopy measurement with a plurality of sensors; for process compensated resonance testing) is illustrated in FIGS. 1 and 2, and is identified by reference numeral 5. The resonance inspection tool 5 includes a computer 10 that provides for control of a synthesizer 12 and an analog to digital converter 11 for each data input channel connected to each receiving or response transducer 22, 24 of the resonance inspection tool 5. Transducer 22 has an output on line 31, while transducer 24 has an output on line 25.

Synthesizer 12 may have a frequency range from greater than 0 to 20 M Hertz. Other frequency ranges may be appropriate. Synthesizer 12 provides two outputs which are the frequency F1 at output 14 and a second output which is the frequency F2 at line 16. In one embodiment, the frequency F2 is either F1 plus a constant frequency such as 1000 Hertz for heterodyne operation of the receiver, or at F1 for homodyne operation. A first transducer 18 (e.g., the input or driving transducer) is excited at a frequency F1 by synthesizer 12. Transducer 18 provides vibration (e.g., ultrasonic) to an object 20 to be tested via resonance inspection.

The response of the object 20 is then received by two separate output transducers 22 and 24. The circuitry from the output transducer 22 and A/D converter 11 can be identical to circuitry between output transducer 24 and A/D converter 11. For this reason, only the circuitry between output transducer 22 and A/D converter 11 will be discussed below. The times one (.times.1) amplifier 26 is connected to the output transducer 22, provides current for transformer 28, and has a feedback 27.

The output of transducer 22 is connected to a receiver 41 (FIG. 2). Receiver 41 is used for the purpose of providing amplification and noise rejection in the circuit between output transducer 22 and A/D converter 11. The output A (line 40) is applied to the A/D converter 11 within the computer 10. The A/D converter 11 provides an A/D conversion for each of lines 40 and 42. The converted information is then entered into a file which consists of the measured frequency, the amplitude of A, the amplitude of B, the amplitude of A plus B, and the amplitude of A minus B. This file is then used for further analysis of the spectrum to determine characteristics of a part 20 being tested.

The times one (.times.1) amplifier 26 provides feedback to an inner coaxial cable shield 30 which surround the lead from transducer 22 to amplifier 26. Shield 30 is another grounded shield which can also be used for noise suppression. The outer surrounding coaxial cable is not shown in FIG. 1. If lead 31 is short, the shield 30 may be omitted because capacitance will not be too large. The purpose of the inner shield 30 is to provide a cancellation of capacitance of the lead 31.

The transformer 28 may be a 4:1 step-down transformer used for impedance matching to the input of amplifier 32. In this regard, it should be noted that the output impedance of amplifier 26 may be much lower than the output impedance of transducer 22. This provides for the power gain and the necessary feedback to shield 30. The amplifier 32 may have a gain factor of 100:1 or a 40 db gain. Other gain factors may be appropriate. The amplifier 26 may be a broad-band amplifier having a band pass on the order of 50 M Hertz.

Mixer 34 has an output signal (e.g., a 1 K Hertz signal) having a magnitude which is proportional to the magnitude of the frequency F1 provided on line 14 from synthesizer 12. The function of the synthesizer 12 is to provide a point-by-point multiplication of instantaneous values of inputs on lines 16 and 33. The mixer 34 also has many high frequency output components which are of no interest. The high frequency components are therefore filtered out by the low-band pass filter 38 which is connected to mixer 34 by line 36. Filter 38 serves to clean-up the signal from mixer 34 and provide a voltage on line 40 which is only the output signal at an amplitude which is proportional to the amplitude of the output 31 of transducer 22.

Operation of the resonance inspection tool 5 will be briefly described in relation to measurement steps performed by measurement of the output of either transducer 22 or transducer 24 controlled by computer 10. A measurement cycle may be initiated, and provides initialization for the frequency F and the desired frequency step. The frequency step may be 1 Hertz or any other frequency selected for the measurement. Although a constant frequency step may be utilized, the frequency step may be determined by any appropriate algorithm. In one embodiment, the frequency step is determined by determining the start frequency and the stop frequency, and dividing the frequency difference by the number of steps desired for the measurement. In any case, the synthesizer 12 is configured to provide a plurality of input or drive frequencies to transducer 18.

Once a signal is picked up by the receiver (i.e., an output on line 33), a pause for ring delay there is a provided. The pause for ring delay may be on the order of 30 milliseconds, although other ring delays can be used if the object under test 20 has resonances that are narrower than a few Hertz. The purpose of the pause is to give the object 20 an opportunity to reach its steady state magnitude in response to a steady input from transducer 18. The pause time is time after the frequency is applied and before detection is initiated.

After the ring delay is complete, analog-to-digital converter 11 provides an output that can be used by the data recording computer. The output of the A/D conversion is then written to a file by the computer 10 for the purpose of analysis of the data by another program. Data comprising the unique signature or characterizing of the object 20 is written into file as it is created. Reading may be stopped when a read frequency is present and step 66 stops the program. Once information is entered into file, subsequent processing can be used to generate a signature or characterize the object 20 such as the resonant magnitudes, the sum of resonant magnitudes, the difference resonant magnitudes, or other manipulations of the multiple channel multiple frequency measurement which is used to perform the unique signature of the object 20. The magnitude of the outputs at each sensor location for each resonance frequency may be compared.

Figure 3:
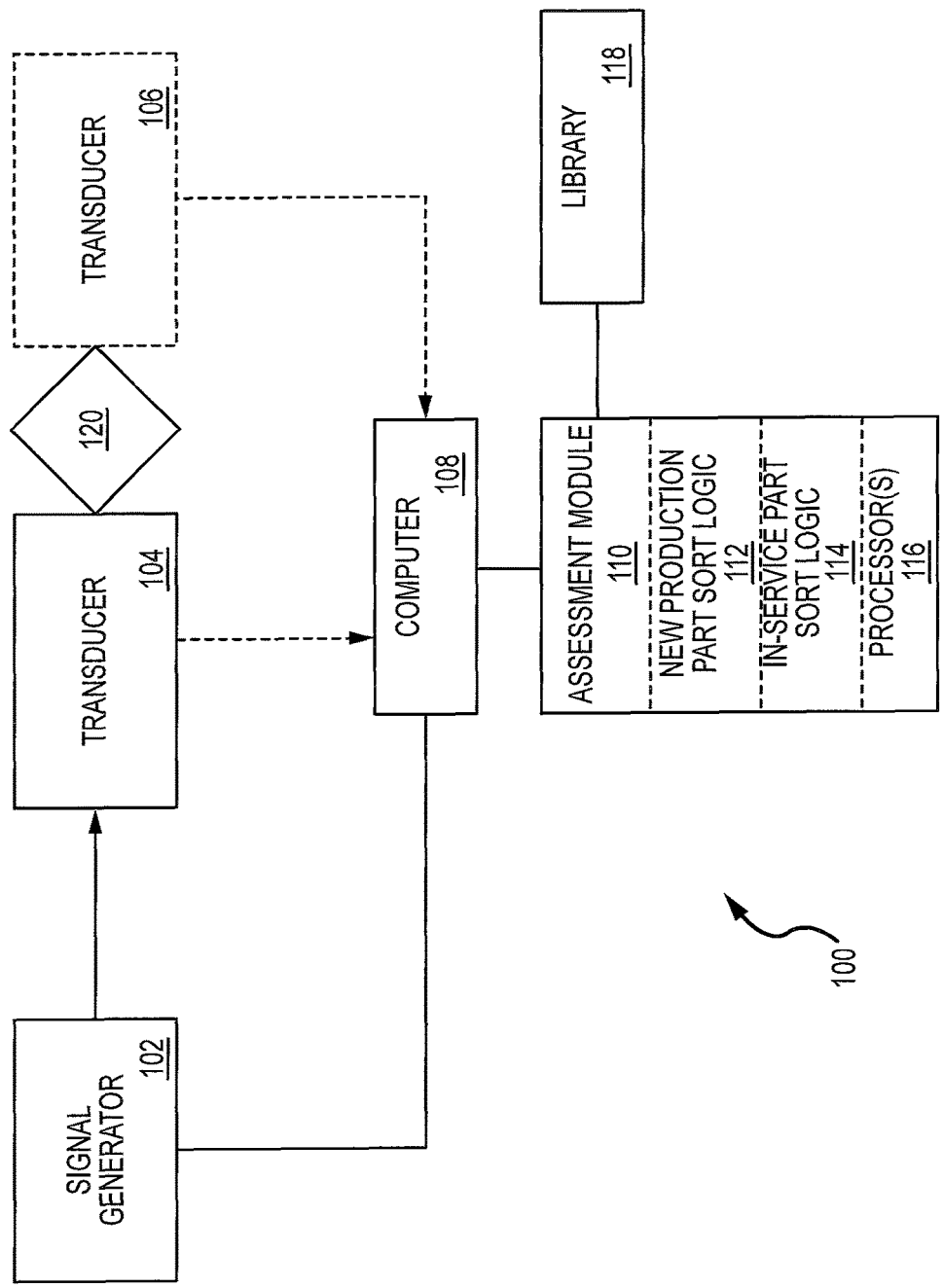
FIG. 3 is a block-diagram of another embodiment of a resonance inspection tool.

Another embodiment of a resonance inspection tool or system is illustrated in FIG. 3 and is identified by reference numeral 100. The resonance inspection tool 100 includes a signal generator 102 of any appropriate type, at least one transducer of any appropriate type that interfaces with a part 120 (e.g. via physical contact) that is to undergo a resonance inspection (e.g., transducer 104), and a computer 108. The computer 108 may include what may be characterized as an assessment module 110 (e.g., incorporated/embodied by a non-transitory computer-readable storage medium). Generally, the assessment module 110 may be configured to evaluate the results of a resonance inspection, for instance for purposes of determining whether the part 120 should be accepted or rejected by the resonance inspection tool 100, determining whether the part 120 is at an end-of-life state or condition, or the like. A part 120 that is "accepted" by the resonance inspection tool 100 may mean that the resonance inspection tool 100 has determined that the part 120 may be put into service (e.g., utilized for its intended purpose(s) and/or used according to its design specifications). In one embodiment, a part 120 that has been accepted by the resonance inspection tool 100 means that the tool 100 has determined that the part 120 is free of defects, is not in an end-of-life condition or state, is aging normally, or any combination thereof. A part 120 that is "rejected" by the resonance inspection tool 100 may mean that the resonance inspection tool 100 has determined that the part 120 should not be put into service (e.g., should not be utilized for its intended purpose(s) and/or should no longer be used according to its design specifications). In one embodiment, a part 120 that has been rejected by the resonance inspection tool 100 means that the tool 100 has determined that the part 120 includes at least one defect, is at or near an end-of-life condition or state, is aging abnormally, or any combination thereof.

A part 120 that is analyzed or assessed by the resonance inspection tool 100 may be of any appropriate size, shape, configuration, type, and/or class. For purposes of the resonance inspection tool 100, there could be two part classes. One part class includes new production parts—newly manufactured parts that have not yet been released from production (e.g., parts that have not been shipped for use by an end user or customer). New production parts include parts that may have undergone at least some post-production testing of any appropriate type (including without limitation a resonance inspection). Another part class includes in-service parts—parts that have been released from production for use in one or more end-use applications. An "in-service part" in the context of the embodiments to be addressed herein encompasses a part that has been used to at least some extent after having been released by the manufacturer. An in-service part may be a part that has been put into use by a party other than the manufacturer (e.g., a customer or end user). Although an in-service part could be used autonomously or independently of any other parts, an in-service part may be incorporated by an assembly or system (e.g., a turbine blade (an in-service part) in a jet engine (an assembly or system)).

The signal generator 102 generates signals that are directed to the transducer 104 for transmission to the part 120 in any appropriate manner/fashion (e.g., via physical contact between the transducer 104 and the part 120). Signals provided by the signal generator 102 are used to mechanically excite the part 120 (e.g., to provide energy to the part 120 for purposes of inducing vibration). Multiple frequencies may be input to the part 120 through the transducer 104 in any appropriate manner. This may be characterized as "sweeping" through a range of frequencies that are each input to the part 120, and this may be done in any appropriate manner for purposes of the resonance inspection tool 100. Any appropriate number/range of frequencies may be utilized, and any appropriate way of progressing through a plurality of frequencies (e.g., a frequency range) may be utilized by the resonance inspection tool 100.

In one embodiment, at least one other transducer 106 is utilized in the resonance inspection of the part 120 using the resonance inspection tool 100 of FIG. 3, including where two transducers 106 are utilized (e.g., in accordance with the embodiment of FIGS. 1 and 2 noted above). Each of the transducers 106, as well as the input or drive transducer 104, may be in physical contact with the part 120. It may be such that the part 120 is in fact entirely supported by the transducer 104 and any additional transducers 106. Each transducer 106 that is utilized by the resonance inspection tool 100 is used to acquire the frequency response of the part 120 to the frequencies input to the part 120 by the drive transducer 104, and therefore each transducer 106 may be characterized as an output or receiver transducer 106.

Another embodiment of the resonance inspection tool 100 of FIG. 3 utilizes only the transducer 104. That is, no additional transducers 106 are utilized by the resonance inspection tool 100 in this case, and therefore the transducer 106 is presented by dashed lines in FIG. 3. In this case, the transducer 104 is used to input a drive signal to the part 120 (e.g., to excite the part 120 at a plurality of different frequencies), and is also used to acquire the frequency response of the part 120 to these input drive frequencies. For instance, a first drive signal at a first frequency (from the signal generator 102) may be transmitted to the part 120 through the transducer 104, the transmission of this first drive signal may be terminated, and the transducer 104 may be used to acquire a first frequency response of the part 120 to this first drive signal (including while a drive signal is being transmitted to the part 120). The signal generator 102 may also be used provide a second drive signal at a second frequency to the transducer 104, which in turn transmits the second drive signal to the part 120, the transmission of this second drive signal may be terminated, and the transducer 104 may once again be used to acquire a second frequency response of the part 120 to this second drive signal (including while a drive signal is being transmitted to the part 120). This may be repeated any appropriate number of times and utilizing any appropriate number of frequencies and frequency values. One or more drive signals may be sequentially transmitted to the part 120 by the signal generator 102 and transducer 104, one or more drive signals may be simultaneously transmitted to the part 120 by the signal generator 102 and transducer 104, or any combination thereof.

The frequency response of the part 120 is transmitted to the computer 108 of the resonance inspection tool 100 of FIG. 3. This computer 108 may be of any appropriate type and/or configuration, and is used by the resonance inspection tool 100 to evaluate the part 120 in at least some fashion (e.g., to determine whether to accept or reject the part 120). Generally, the part 120 is vibrated by the transducer 104 according to a predetermined signal(s), and the part 120 is evaluated by the resulting vibrational response of the part 120. For instance, this evaluation may entail assessing the part 120 for one or more defects of various types, assessing whether the part 120 is at or near the end of its useful, life, assessing whether the part 120 is aging normally or abnormally, or any combination thereof.

The computer 108 may incorporate and utilize the above-noted assessment module 110 to evaluate the response of the part 120 to a resonance inspection. The assessment module 110 may be of any appropriate configuration and may be implemented in any appropriate manner. In one embodiment, the assessment module 110 includes at least one new production part sort logic 112 (e.g., logic configured to determine whether to accept or reject new production parts; incorporated/embodied by a non-transitory computer-readable storage medium), at least one in-service part sort logic 114 (e.g., logic configured to determine whether to accept or reject in-service parts; incorporated/embodied by a non-transitory computer-readable storage medium), along with one or more processors 116 of any appropriate type and which may be implemented in any appropriate manner. The assessment of the response of the part 120 to the input drive signals may entail comparing the response to a library 118 utilized by the resonance inspection tool 100. This library 118 may be stored on a computer-readable storage medium of any appropriate type or types and in a non-transitory form (e.g., a non-transitory computer-readable storage medium), including without limitation by using one or more data storage devices of any appropriate type and disposed in any appropriate arrangement.

Figure 4:
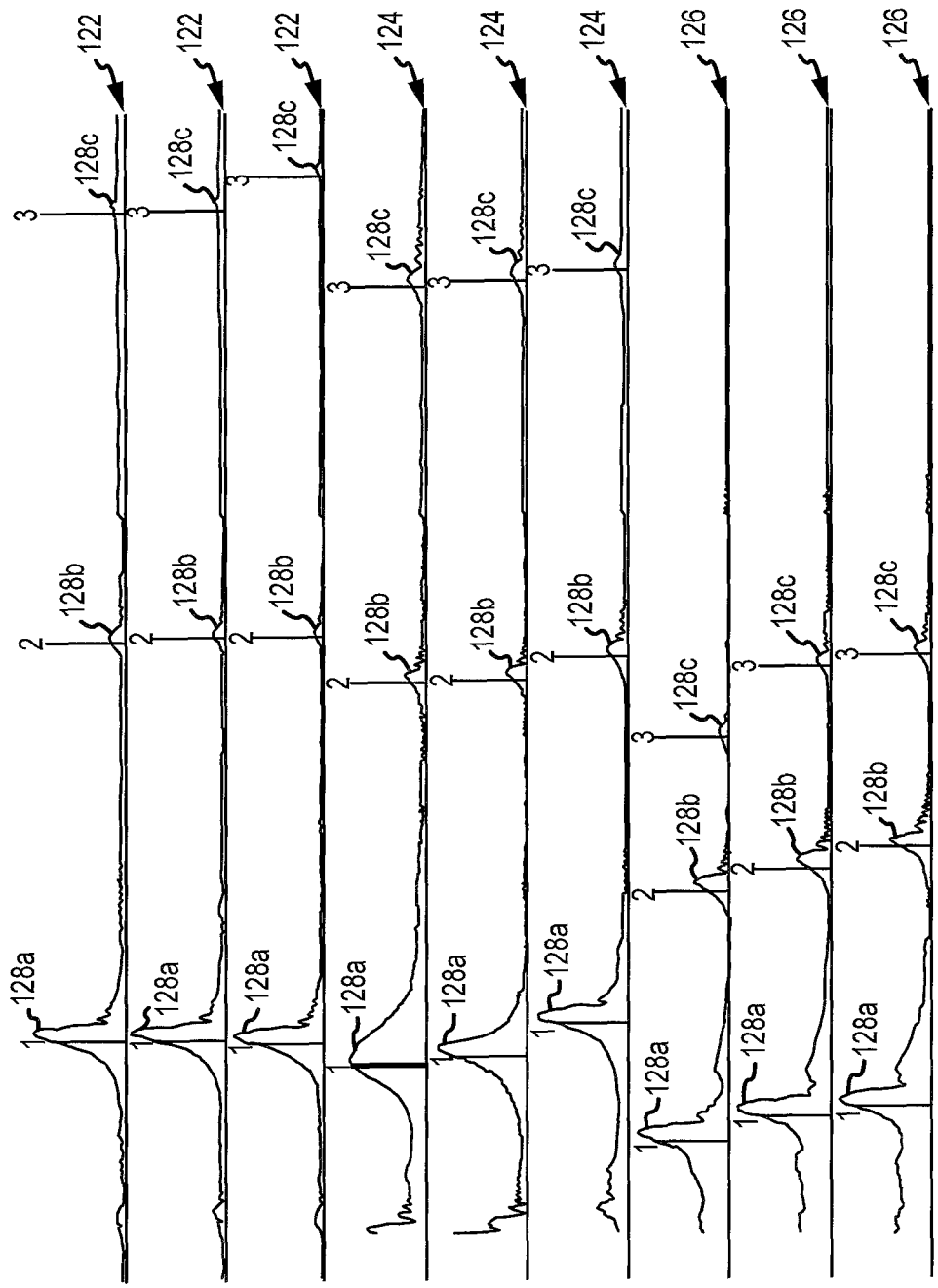
FIG. 4 presents various resonance inspection results of parts that may be included in the library utilized by the resonance inspection tool of FIG. 3.

The library 118 of the resonance inspection tool 100 may include various types of resonance inspection results to allow the resonance inspection tool 100 to assess a part 120. Generally, the resonance inspection results from the part 120 are compared with data in the library 118 from at least one other part that is the same as the part 120 in one or more respects (e.g., a part 120 in the form of a turbine blade will be compared to turbine blade data in the library 118; a part 120 in the form of a turbine blade will not be compared with ball bearing data in the library 118). Representative resonance inspection results are presented in FIG. 4, and are of a type that may be included in the library 118. The three spectra 122 shown in FIG. 4 represent the frequency response of a new production part 120 to a certain input frequency, and where this new production part 120 has been accepted by the resonance inspection tool 100. Note how the three peaks 128a, 128b, and 128c differ in at least one respect between the various spectra 122, but yet the corresponding new production part 120 is acceptable in all three instances.

The three spectra 124 shown in FIG. 4 represent the frequency response of an in-service part 120 to a certain input frequency, and where this in-service part 120 has been accepted by the resonance inspection tool 100. Note how the three peaks 128a, 128b, and 128c in the spectra 124 differ in at least one respect from the corresponding peaks 128a, 128b, and 128c in the spectra 122 (again, associated with a new production part 120).

The three spectra 126 shown in FIG. 4 represent the frequency response of an in-service part 120 to a certain input frequency, and where this in-service part 120 has been rejected by the resonance inspection tool 100. Note how the three peaks 128a, 128b, and 128c in the spectra 126 differ in at least one respect from the corresponding peaks 128a, 128b, and 128c in the spectra 124 (again, associated with an in-service part 120 that the resonance inspection tool 100 would accept). Generally, each of the peaks 128a, 128b, and 128c in the spectra 126 has shifted to the left compared to the corresponding peaks 128a, 128b, and 128c in the spectra 122 and 124. Moreover, note the "compression" between the peaks 128a, 128b in the spectra 126 compared to the spectra 122, 124, as well as the "compression" between the peaks 128b, 128c in the spectra 126 compared to the spectra 122, 124.

Figure 5:
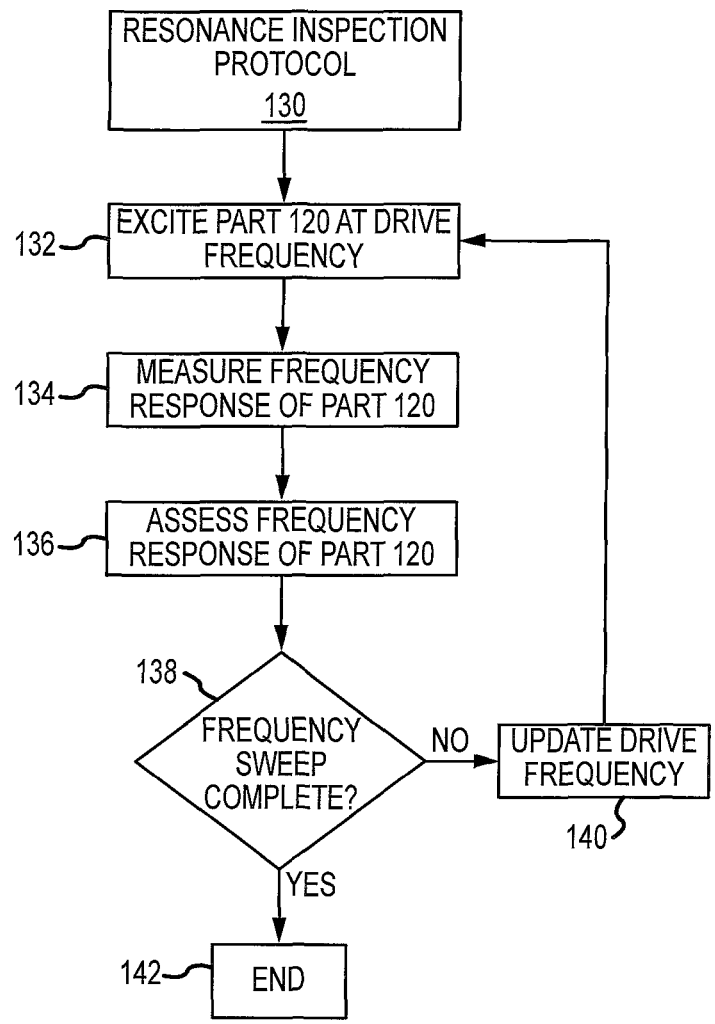
FIG. 5 is one embodiment of a resonance inspection protocol that may be utilized by a resonance inspection tool.

One embodiment of a resonance inspection protocol that may be utilized by the resonance inspection tool 100 of FIG. 3 is presented in FIG. 5 and is identified by reference numeral 130. Step 132 of the resonance inspection protocol 130 is directed to exciting a part 120 at a drive frequency (e.g. via a signal from the signal generator 102 that is input to the part 120 through the transducer 104). The response of the part 120 is obtained or measured pursuant to step 134 (e.g., via one or more transducers 106; via the transducer 104 in a single transducer configuration). It should be appreciated that steps 132 and 134 may be executed in at least partially overlapping relation (e.g., the frequency response of the part 120 could be obtained as a drive signal is being applied to the part 120), although steps 132 and 134 could be sequentially executed as well.

The frequency response of the part 120 is assessed pursuant to step 136 of the resonance inspection protocol 130. Step 138 of the protocol 130 is directed to determining if the frequency sweep is complete—whether each of the desired drive frequencies has been input to the part 120. If not, the protocol 130 proceeds to step 140, and which is directed to updating or changing the drive frequency to be input to the part 120. Control is then returned to step 132 for repetition in accordance with the foregoing. Once the part 120 has been driven at each of the desired frequencies, the protocol 130 is terminated pursuant to step 142.

Step 136 of the resonance inspection protocol 130 is again directed to assessing the response (e.g., frequency) of the part 120 (e.g., using the sort logic 112 or 114 and/or comparing the response of the part 120 to the library 118 of the resonance inspection tool 100). This assessment may be undertaken at any appropriate time and in any appropriate manner. For instance, the assessment associated with step 136 could be undertaken while the part 120 continues to be driven by a signal at one or more frequencies. Another option is for the assessment provided by step 136 to be undertaken only after all drive signals have been input to the part 120 (step 132), after the all frequency responses have been obtained (step 134), or both.

A frequency response for a part, as described herein and including for purposes of step 136 of the resonance inspection protocol 130 of FIG. 5, may actually be in the form of a plot or compilation of a collection of responses of a part-under-test (e.g., part 120) at each frequency that may be used to drive the part-under-test. For instance, if a part-under-test is driven at frequency $f_1$, the amplitude of the response of the part-under-test at this same frequency $f_1$ may be included in the noted plot at the frequency $f_1$; if the part-under-test is driven at frequency $f_2$, the amplitude of the response of the part-under-test at this same frequency $f_2$ may be included in the plot at the frequency $f_2$; if the part-under-test is driven at frequency $f_3$, the amplitude of the response of the part-under-test at this same frequency $f_3$ may be included in the plot at this frequency $f_3$; and so forth. Any such plot is within the scope of a "frequency response" as set forth herein.

Figure 6:
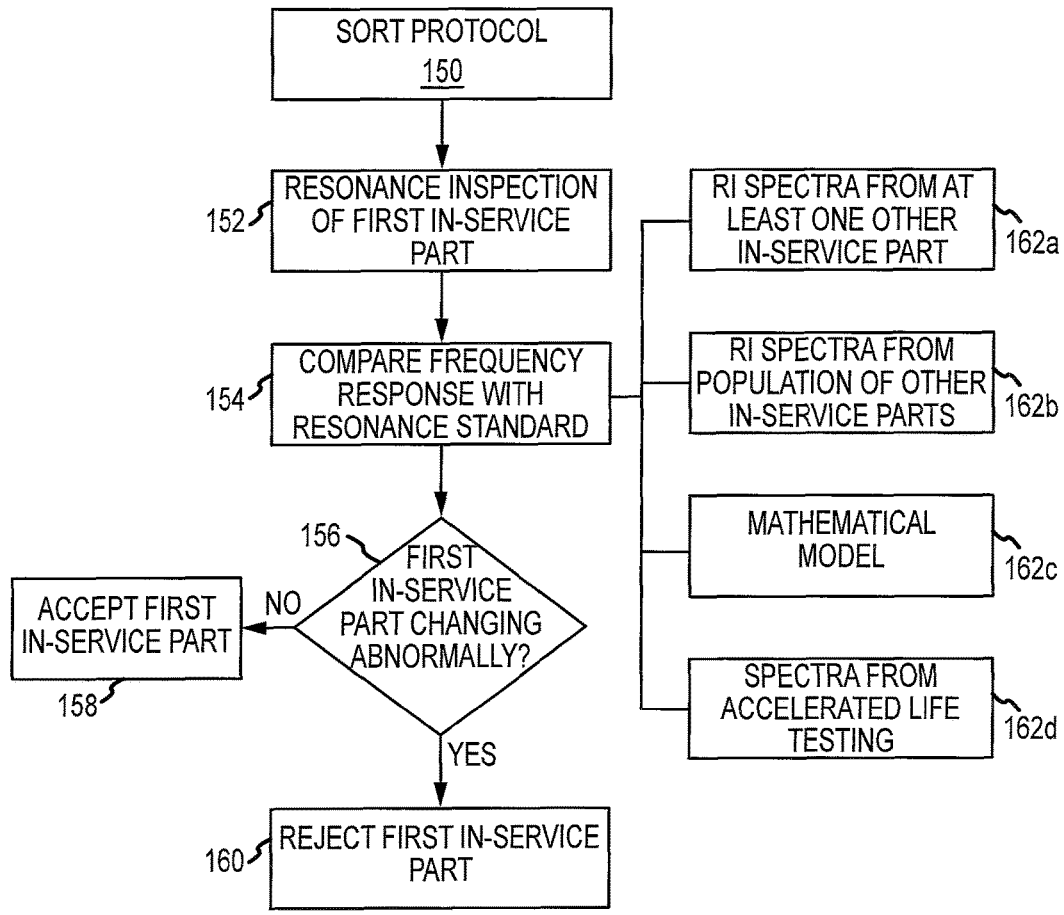
FIG. 6 is one embodiment of an in-service part sort protocol that may be utilized by a resonance inspection tool.

One embodiment of a sort protocol is presented in FIG. 6 and is identified by reference numeral 150. The sort protocol 150 may be utilized by the in-service part sort logic 114 of the resonance inspection tool 100 shown in FIG. 3, and is configured for the assessment of in-service parts. Generally, the sort protocol 150 is directed to determining whether or not an in-service part is experiencing normal changes while in service. Stated another way, the sort protocol 130 may be characterized as being directed to determining whether an in-service part is aging normally or abnormally and via a resonance inspection. Each resonance inspection of an in-service part may be conducted while the in-service part remains in an installed state or condition (e.g., in situ) for purposes of the sort protocol 150. Alternatively, each resonance inspection of an in-service part may be conducted with the in-service part being in an uninstalled state or condition (e.g., after having been removed from an assembly incorporating the same) for purposes of the sort protocol 150.

A resonance inspection of a first in-service part (e.g., part 120 shown in FIG. 3) is conducted pursuant to step 152 of the sort protocol 150 of FIG. 6 (e.g., via execution of the resonance inspection protocol 130 of FIG. 5). The frequency response of the first in-service part is compared with a resonance standard pursuant to step 154. This "resonance standard" may be incorporated by the library 118 used by the resonance inspection tool 100 (FIG. 3) and/or may be utilized by the in-service part sort logic 114, and in any case may characterize or define what should be a "normal change" for a predetermined in-service part (e.g., to determine whether the first in-service part is changing or aging in a normal manner or fashion). That is, the comparison of step 154 is undertaken for purposes of determining whether the first in-service part is changing normally or abnormally (step 156). If the comparison with the resonance standard (step 154) determines that the first in-service part is changing abnormally, the sort protocol 150 proceeds from step 156 to step 160. A first in-service part that is changing abnormally may be rejected by the sort protocol 150 pursuant to step 160 (e.g., the first in-service part may be designated to be taken out of service). A first in-service part that is changing normally is accepted by the sort protocol 150 pursuant to step 158 (e.g., the first in-service part may be returned to service).

The resonance standard associated with step 154 may include actual and/or projected/predicted resonance inspection results. Moreover, these resonance inspection results may be from various points in time over the life cycle of a part (e.g., resonance inspection results when in the form of a new production part, resonance inspection results at or associated with 5,000 cycles of usage, resonance inspection results at or associated with 10,000 cycles of usage, resonance inspection results at or associated with 15,000 cycles of usage, and so forth). Step 156 of the sort protocol 150 may or may not take usage data (e.g., hours or cycles of operation) into account when assessing a particular in-service part. For instance, step 156 could be configured so that resonance inspection results from the in-service part being assessed via the sort protocol 150 would have to "match" data in the resonance standard having the same or comparable usage data (e.g., if the in-service part that was being assessed via the sort protocol 150 was at 10,000 cycles of usage, step 156 could be configured such that resonance inspection results from this in-service part would have to match data in the resonance standard that are also associated with 10,000 cycles of usage). Step 156 could also be configured so that resonance inspection results from the in-service part being assessed via the sort protocol 150 would only need to "match" data in the resonance standard, regardless of any associated usage data (e.g., step 156 could be configured to determine that a part at 10,000 cycles was changing normally, even though its resonance inspection results "matched" data in the resonance standard that was in fact associated with 20,000 cycles).

The resonance standard associated with step 154 of the sort protocol 150 of FIG. 6 may be of various forms. Representative resonance standards are shown in FIG. 6. The resonance standard for step 154 may be in the form of: 1) spectra from one or more other in-service parts (e.g., spectra from a resonance inspection previously conducted on one or more in-service parts other than that being inspected pursuant to the sort protocol 150 (box 162*a*); 2) one or more spectra from a population of other in-service parts (box 162*b*); 3) resonance inspection results predicted and/or derived via mathematical modeling (box 162*c*); and 4) spectra obtained from accelerated life testing (box 162*d*).

The resonance standard associated with step 154 of the sort protocol 150 could be in the form of any one or more of the type of spectra 124 shown in FIG. 4 (e.g., box 162*a*). If the resonance inspection results from the resonance inspection conducted pursuant to step 152 matched or complied with any of these spectra 124 in one or more respects, the in-service part could be accepted by step 158 of the sort protocol 150.

The resonance standard used by step 154 of the sort protocol 150 may be based upon a population of in-service parts (box 162*b*). This population of in-service parts does not need to include the first in-service part that is being assessed by the sort protocol 150. The population of in-service parts may be viewed as a "peer group" for purposes of assessing the first in-service part via the sort protocol 150 (e.g., other parts manufactured in accordance with common specifications and/or that are functionally interchangeable with the first in-service part). For instance, the resonance standard may be in the form of spectra (e.g., spectra 124 from FIG. 4) from each of a plurality of in-service parts that are within the population. If the comparison of step 154 determines that the resonance inspection results from the first in-service part (step 152) match or comply with any of these spectra from the population in one or more respects, the first in-service part may be accepted pursuant to step 158 of the sort protocol 150. The resonance standard associated with step 154 may also be in the form of an average of spectra from each of a plurality of in-service parts that are within the noted population. If the comparison of step 154 determines that the resonance inspection results (step 152) match or comply with this spectral average from the population in one or more respects, the first in-service part may be accepted pursuant to step 158 of the sort protocol 150.

The resonance standard associated with step 154 of the sort protocol 150 may also be provided by mathematical modeling (box 162*c*). This mathematical modeling may be used to generate resonance inspection results for various times over the life of a part that is changing normally. If the comparison of step 154 determines that the resonance inspection results (step 152) match or comply with any of these mathematically derived resonance inspection results in one or more respects, the first in-service part may be accepted pursuant to step 158 of the sort protocol 150.

The resonance standard associated with step 154 of the sort protocol 150 may also be provided by accelerated life testing (box 162*d*). Resonance inspection results may be acquired as a part undergoes accelerated life testing, and these resonance inspection results may be used by the resonance standard associated with step 154. If the comparison of step 154 determines that the resonance inspection results (step 152) match or comply with any of the resonance inspection results acquired during the accelerated life testing in one or more respects, the first in-service part may be accepted pursuant to step 158 of the sort protocol 150.

Figure 7:
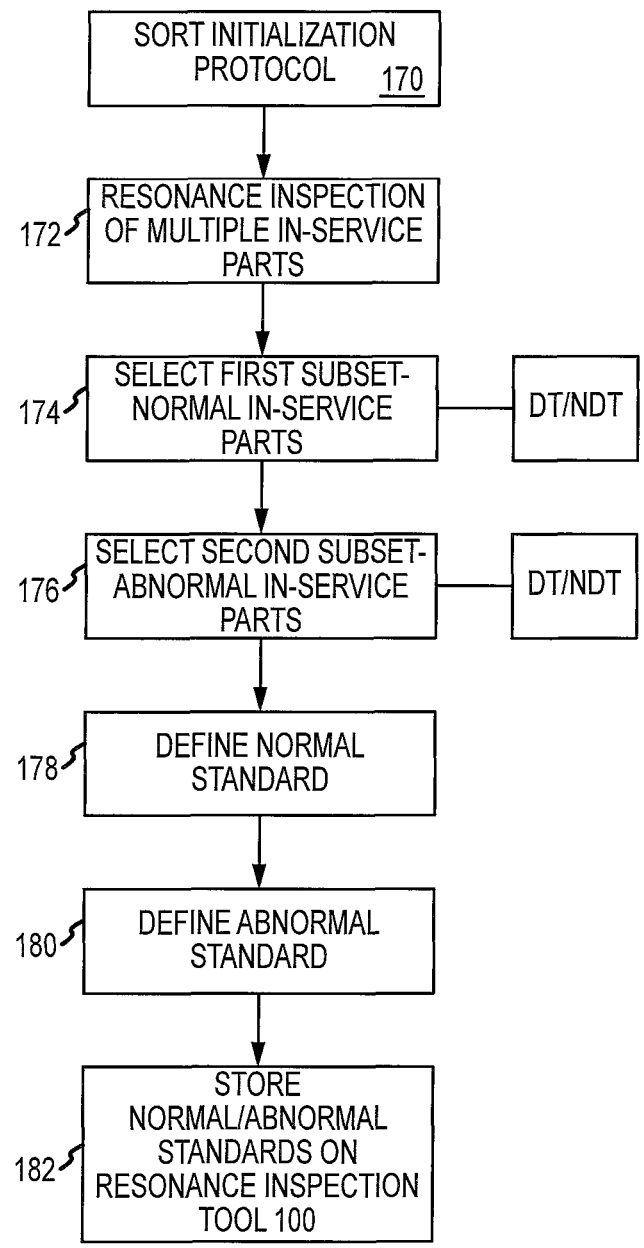
FIG. 7 is one embodiment of an in-service part sort initialization protocol that may be utilized by a resonance inspection tool.

One embodiment of a sort initialization protocol is presented in FIG. 7 and is identified by reference numeral 170. The sort initialization protocol 170 may be utilized by and/or to configure the in-service part sort logic 114 of the resonance inspection tool 100 shown in FIG. 3, and is thereby associated with the assessment of in-service parts (e.g., logic configured to determine whether an in-service part should be rejected or accepted). A resonance inspection of a plurality of in-service parts (e.g., part 120 shown in FIG. 3) is conducted pursuant to step 172 of the sort initialization protocol 170 of FIG. 7 (e.g., via execution of the resonance inspection protocol 130 of FIG. 5). A first subset of "normal" in-service parts (that underwent resonance inspection pursuant to step 172) is defined pursuant to step 174. A determination as to whether or not a given in-service part from step 172 is "normal" for purposes of step 174 may be undertaken in any appropriate manner, for instance using destructive testing, nondestructive testing, and/or a combination thereof.

A second subset of "abnormal" in-service parts (that underwent resonance inspection pursuant to step 172) is defined pursuant to step 176 of the sort initialization protocol 170. A determination as to whether or not a given in-service part from step 172 is "abnormal" for purposes of step 176 may be undertaken in any appropriate manner, for instance using destructive testing, nondestructive testing, or a combination thereof. In one embodiment, an in-service part that undergoes a resonance inspection pursuant to step 172 is characterized as normal (step 174) or abnormal (step 176) other than by the results of the resonance inspection associated with step 172 (e.g., via DT and/or NDT).

One or more destructive testing techniques may be used, one or more nondestructive testing techniques may be used, or both, in relation to each of steps 174 and 176 of the sort initialization protocol 170 of FIG. 7. Representative nondestructive testing techniques that may be used in relation to each of steps 174 and 176 includes without limitation visual inspection, microscopy, magnetic particle, penetrant, eddy current, x-ray, computed tomography, flash thermography, ultrasound, sonic infra-red, phased array, or the like. Representative destructive testing techniques that may be used in relation to each of steps 174 and 176 includes without limitation fatigue testing, static testing, thermal testing, metalography, sectioning, ablation, chemical reduction, or the like.

Step 178 of the sort initialization protocol 170 of FIG. 7 is directed to defining a normal standard, while step 180 of the protocol 170 is directed to defining an abnormal standard. The normal standard associated with step 178 may be defined by one or more of the in-service parts associated with step 174 and may utilize results of the corresponding resonance inspection from step 172 (e.g., spectra of each in-service part within the first subset could be used by the normal standard; an average spectra from a plurality of in-service parts within the first subset could be used by the normal standard). Similarly, the abnormal standard associated with step 180 may be defined by one or more of the in-service parts associated with step 176 and may utilize results of the corresponding resonance inspection from step 172 (e.g., spectra of each in-service part within the second subset could be used by the abnormal standard; an average spectra from a plurality of in-service parts within the second subset could be used by the abnormal standard). Both the normal standard (178) and the abnormal standard (step 180) may be stored (e.g., on a computer-readable storage medium) for use by the resonance inspection tool 100 through execution of step 182 of the sort initialization protocol 170 (e.g., included in the library 118 shown in FIG. 3).

Figure 8:
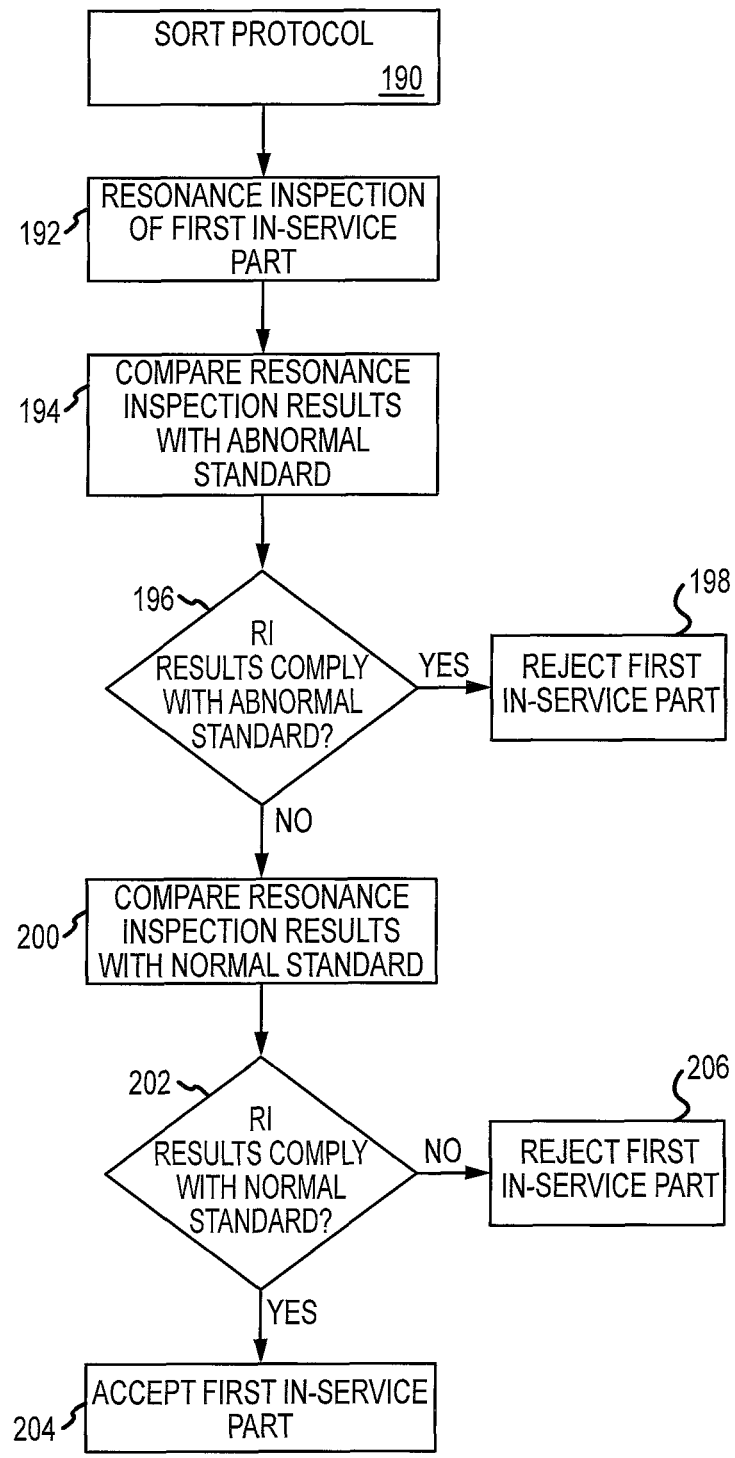
FIG. 8 is one embodiment of an in-service part sort protocol that may be utilized by a resonance inspection tool, including in conjunction with the sort initialization protocol of FIG. 7.

Another embodiment of a sort protocol is presented in FIG. 8 and is identified by reference numeral 190. The sort protocol 190 may be utilized by the in-service part sort logic 114 of the resonance inspection tool 100 shown in FIG. 3, and is configured for the assessment of in-service parts. The resonance inspection of an in-service part may be conducted while the in-service part remains in an installed state or condition (e.g., in situ) for purposes of the sort protocol 190. Alternatively, the resonance inspection of an in-service part may be conducted with the in-service part being in an uninstalled state or condition (e.g., after having been removed from an assembly incorporating the same) for purposes of the sort protocol 190.

A resonance inspection of a first in-service part (e.g., part 120 shown in FIG. 3) is conducted pursuant to step 192 of the sort protocol 190 of FIG. 8 (e.g., via execution of the resonance inspection protocol 130 of FIG. 5). Results of the resonance inspection from step 192 may be compared with an abnormal standard (step 194). The abnormal standard associated with steps 194 and 196 may be provided by the sort initialization protocol 170 of FIG. 7. In any case, step 196 of the sort protocol 190 is directed to determining if resonance inspection results (step 192) comply with the abnormal standard. The first in-service part is rejected if the resonance inspection results (step 192) do in fact comply with the abnormal standard (step 198).

Results of the resonance inspection may be compared with a normal standard (step 200). Step 202 is directed to determining if resonance inspection results (step 192) comply with the normal standard. The normal standard associated with steps 200 and 202 may be provided by the sort initialization protocol 170 of FIG. 7. In any case, the first in-service part is accepted if resonance inspection results (step 192) do in fact comply with the normal standard (step 204). The first in-service part is rejected if resonance inspection results (step 192) do not comply with the normal standard (step 206) in the illustrated embodiment.

The protocol 190 may be configured to execute steps 194 and 200 in an order different from that shown in FIG. 8. Consider the case where the protocol 190 is configured to execute step 200 (comparison with a normal standard) before step 194 (comparison with an abnormal standard). If through execution of step 202 a determination is made that resonance inspection results (step 192) do in fact comply with the normal standard, steps 194 and 196 could then be executed. If through execution of step 196 a determination is made that resonance inspection results (step 192) do not comply with the abnormal standard, the protocol 190 could then proceed to the execution of step 204 (where the first in-service part is accepted by the resonance inspection tool 100). However, if a determination was made that the resonance inspection results (step 192) comply with the abnormal standard pursuant to step 196, steps 202 and 196 of the protocol 190 would be providing inconsistent results. In this case, the sort protocol 190 could be configured to reject the first in-service part (step 198)—even through resonance inspection results of the first in-service part were determined by the resonance inspection tool 100 to comply with the normal standard (step 202).

The sort protocol 190 could also be configured to address a condition when resonance inspection results from step 194 do no match either the normal standard (step 200) or the abnormal standard (step 196). One option would be to associate the first in-service part with an unknown condition, and to thereafter further assess the first in-service part. The results of this further analysis could be used to update either the abnormal standard or the normal standard, depending upon whether the first in-service part was determined to be normal or abnormal.

Figure 9:
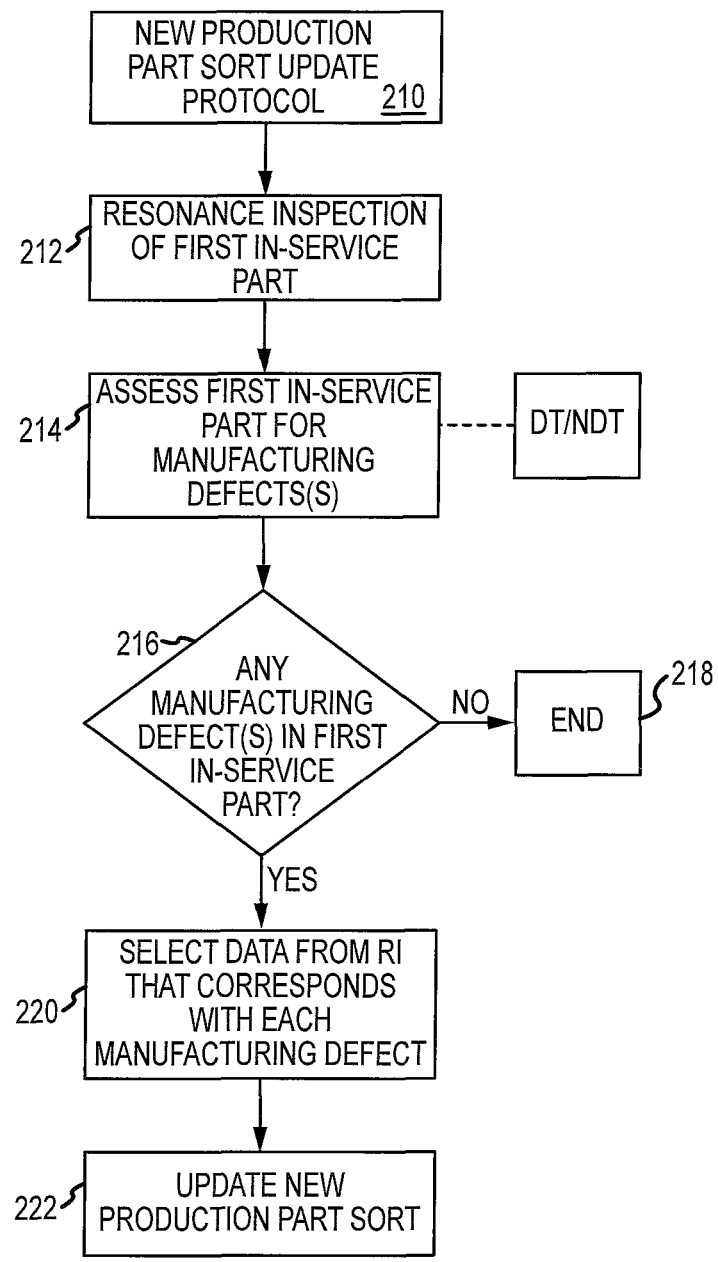
FIG. 9 is one embodiment of a new production part sort update protocol that may be utilized by a resonance inspection tool.

One embodiment of a new production part sort update protocol is presented in FIG. 9 and is identified by reference numeral 210. The sort update protocol 210 may be utilized by the new production part sort logic 112 of the resonance inspection tool 100 shown in FIG. 3. Generally, the sort update protocol 210 of FIG. 9 is configured to assess one or more in-service parts, and utilizes this assessment for purposes of updating the new production part sort logic 112 of the resonance inspection tool 100. The resonance inspection of an in-service part may be conducted while the in-service part remains in an installed state or condition (e.g., in situ) for purposes of the sort update protocol 210. Alternatively, the resonance inspection of an in-service part may be conducted with the in-service part being in an uninstalled state or condition (e.g., after having been removed from an assembly incorporating the same) for purposes of the sort update protocol 210.

A resonance inspection of a first in-service part (e.g., part 120 shown in FIG. 3) is conducted pursuant to step 212 of the sort update protocol 210 of FIG. 9 (e.g., via execution of the resonance inspection protocol 130 of FIG. 5). The first in-service part is assessed for any manufacturing defects pursuant to step 214 of the sort update protocol 210. Any appropriate technique or combination of techniques may be used to determine whether or not the first in-service part has one or more manufacturing defects (e.g., via destructive testing and/or nondestructive testing). If no manufacturing defects are identified in the first in-service part, the sort update protocol proceeds from step 216 to step 218, which terminates the protocol 210. However, if at least one manufacturing defect is identified in the first in-service part (through execution of step 214), the sort update protocol 210 proceeds from step 216 to step 220. Pursuant to step 220, data from the resonance inspection (step 212) that corresponds with a given manufacturing defect is selected. This may be done in relation to each manufacturing defect that is identified in the first in-service part through execution of step 214. The data from the resonance inspection that corresponds with a manufacturing defect may then be used to update the new production part sort logic 112 for the resonance inspection tool 100 of FIG. 3. For instance, the library 118 of the resonance inspection tool 100 may be updated such that new production parts that originally would have been accepted by the resonance inspection tool 100 (prior to execution of the sort update protocol 210) will now be rejected by the resonance inspection tool 100 if any such new production part includes a manufacturing defect that has been identified through execution of the sort update protocol 210 of FIG. 9.

Figure 10:
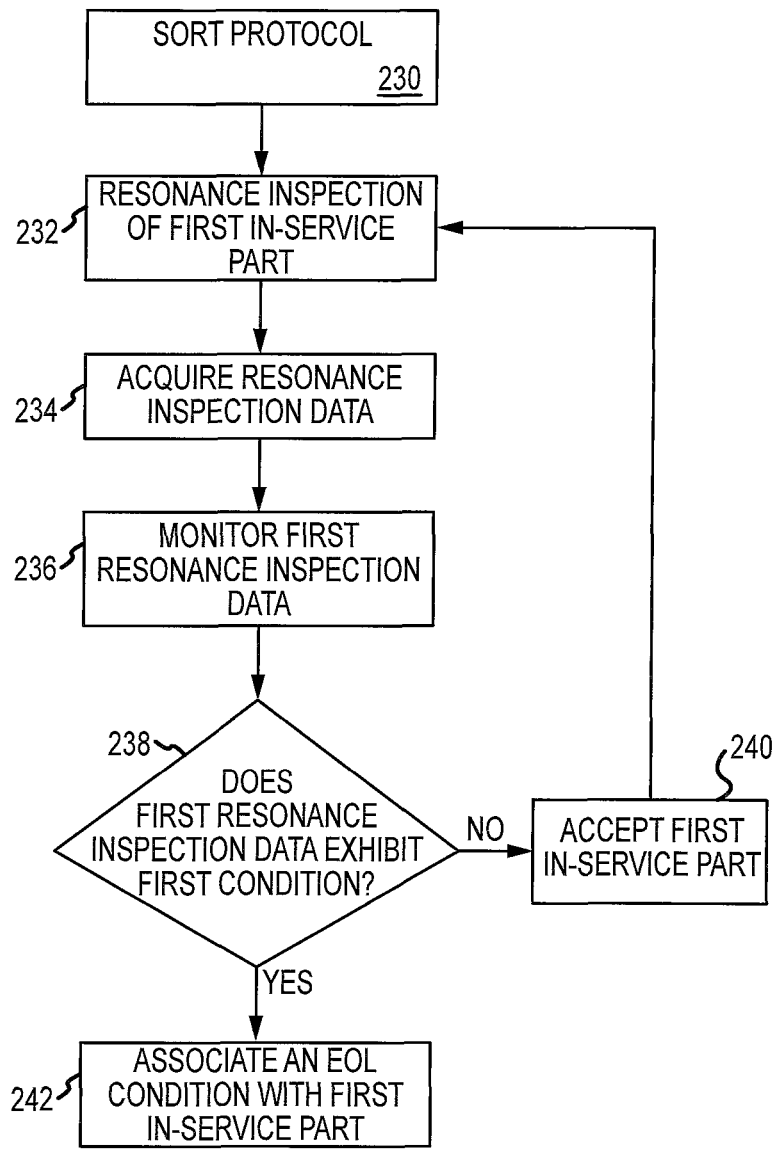
FIG. 10 is another embodiment of an in-service part sort protocol that may be utilized by a resonance inspection tool.

Another embodiment of a sort protocol is presented in FIG. 10 and is identified by reference numeral 230. The sort protocol 230 may be utilized by the in-service part sort logic 114 of the resonance inspection tool 100 shown in FIG. 3, and is configured for the assessment of in-service parts. The resonance inspection of an in-service part may be conducted while the in-service part remains in an installed state or condition (e.g., in situ) for purposes of the sort protocol 230. Alternatively, the resonance inspection of an in-service part may be conducted with the in-service part being in an uninstalled state or condition (e.g., after having been removed from an assembly incorporating the same) for purposes of the sort protocol 230.

The sort protocol 230 is generally directed to monitoring in-service parts for an end-of-life ("EOL") state or condition based upon resonance inspections of the in-service part that are conducted over time. Spaced-in-time resonance inspections of an in-service part may be conducted on any appropriate basis. For instance, an in-service part could be scheduled for a resonance inspection based upon time (e.g., on a calendar quarterly basis), based upon usage/usage data (e.g., hours of operation; cycles of operation), or the like. In one embodiment, an in-service part is scheduled for a resonance inspection based upon what may be characterized as a "cycle target." Such a "cycle target" could be in the form of the in-service part being within a range of cycles, having been used for a minimum number of cycles, or the like.

A resonance inspection of a first in-service part (e.g., part 120 shown in FIG. 3) is conducted pursuant to step 232 of the sort protocol 230 of FIG. 10 (e.g., via execution of the resonance inspection protocol 130 of FIG. 5). Resonance inspection data (e.g., the frequency response of the first in-service part) is acquired pursuant to step 234. The acquisition of resonance inspection data from step 234 may be characterized as being part of the resonance inspection associated with step 232.

Step 236 of the sort protocol 230 is directed to the monitoring first resonance inspection data. More specifically, step 236 is directed to monitoring first resonance inspection data for an occurrence of a first condition. This "first condition" may be in the form of a certain time-rate-of-change in the first resonance inspection data, and will be discussed in more detail below. In the event the first resonance inspection data does not exhibit a first condition, the sort protocol 230 proceeds from step 238 to step 240. As the first condition was not identified in the first resonance inspection data, step 240 is directed to accepting the first in-service part. For instance, the protocol 230 may designate the first in-service part as being appropriate for further service. Another resonance inspection of the first in-service part may be conducted at a later time (e.g., after the expiration of a designated number of hours of operation or cycles of operation). As such, step 240 may return control to step 232 of the sort protocol 230 for repetition in accordance with the foregoing. Since a subsequent resonance inspection will typically be conducted at a later point in time, step 240 could also terminate the protocol 230 (e.g., an "end" step, and such that the protocol 230 would be re-run for each resonance inspection of the first in-service part).

In the event the sort protocol 230 identifies an occurrence of a first condition (e.g., via steps 236 and/or 238), the protocol 230 proceeds from step 238 to step 242. Step 242 is directed to associating an "end-of-life" or EOL condition or state with the first in-service part. This may entail designating the first in-service part for retirement such that the first in-service part is not returned to service.

The first resonance inspection data (step 236) may be characterized as being part of and/or embodied by the resonance inspection data (step 234). In one embodiment, the first resonance inspection data (step 236) may be only part and/or may relate to only part of the resonance inspection data (step 234). The first resonance inspection data (step 236) may also be characterized as being based upon and/or derived from the resonance inspection data (step 234).

The first resonance inspection data (step 236) may be in the form of a frequency shift in the resonance inspection data (step 234) over time. The first resonance inspection data (step 236) may be in the form of: 1) a relative shift of at least one peak in the resonance inspection data acquired from multiple resonance inspections of the first in-service part (e.g., a shift of a first peak in the resonance inspection data relative to a second peak in the resonance inspection data); 2) an absolute shift of at least one peak in the resonance inspection data acquired from multiple resonance inspections of the first in-service part (e.g., a shift of a first peak in the resonance inspection data); 3) an appearance of at least one peak in the resonance inspection data acquired from multiple resonance inspections of the first in-service part; and 4) a disappearance of at least one peak in the resonance inspection data acquired from multiple resonance inspections of the first in-service part.

The "first condition" associated with step 238 may be characterized as being directed to a time-rate-of-change in resonance inspection results from resonance inspection to resonance inspection. That is, one or more parameters embodied by and/or relating to the resonance inspection results may be monitored from resonance inspection to resonance inspection to assess any corresponding change that may be occurring in relation to any such parameter. A certain change in any such parameter may be characterized as an occurrence of the first condition (step 238).

Figure 11:
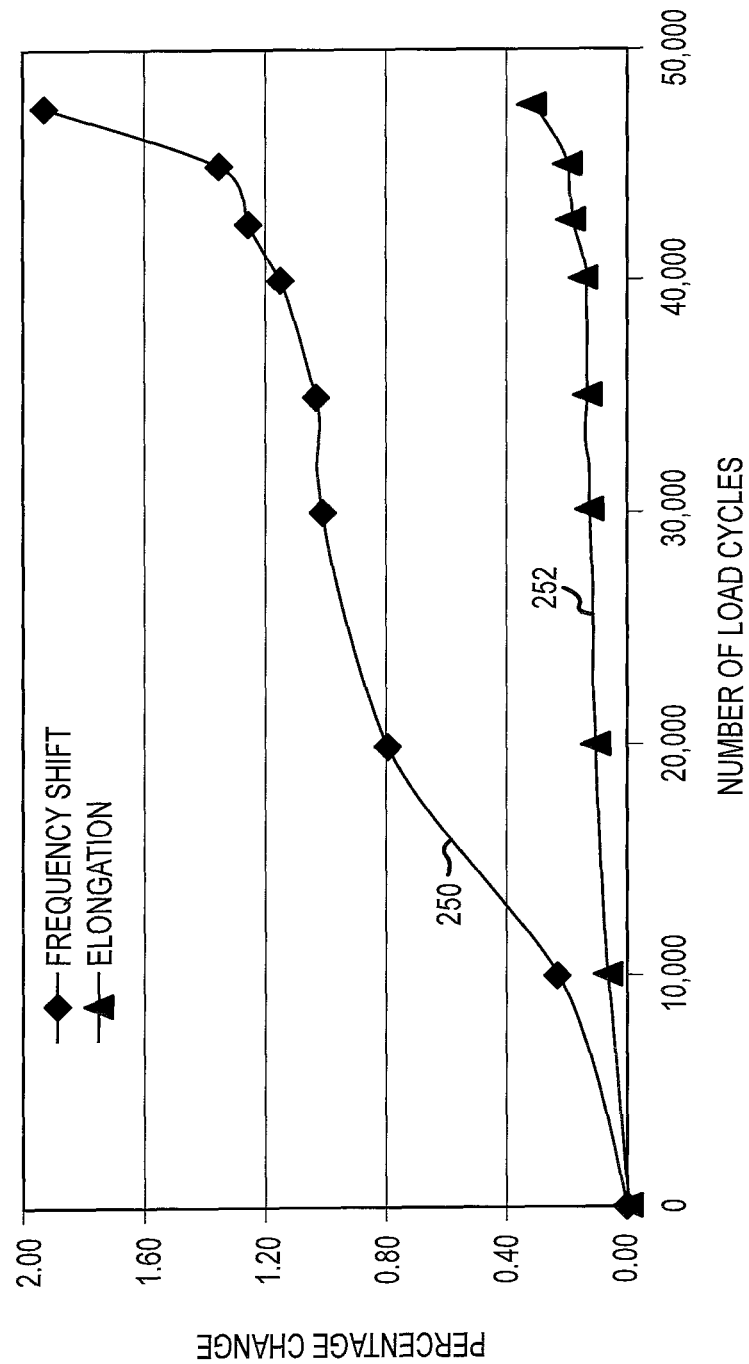
FIG. 11 illustrates a time-rate-of-change of resonance inspection results that may be used by the in-service part sort protocol of FIG. 10.

FIG. 11 illustrates representative first resonance inspection data that may be utilized by the sort protocol 230 of FIG. 10. Plot 250 may be in the form of a frequency shift of a certain peak in the resonance inspection results from resonance inspection to resonance inspection (the "diamonds" being data points obtained from different resonance inspections over time). Plot 252 may be in the form of an "elongation" between a pair of peaks in the resonance inspection results from resonance inspection to resonance inspection (the "triangles" being data points obtained from different resonance inspections over time). "Elongation" means that the spacing between a pair of peaks in the resonance inspection results is being monitored for increases.

Figure 12:
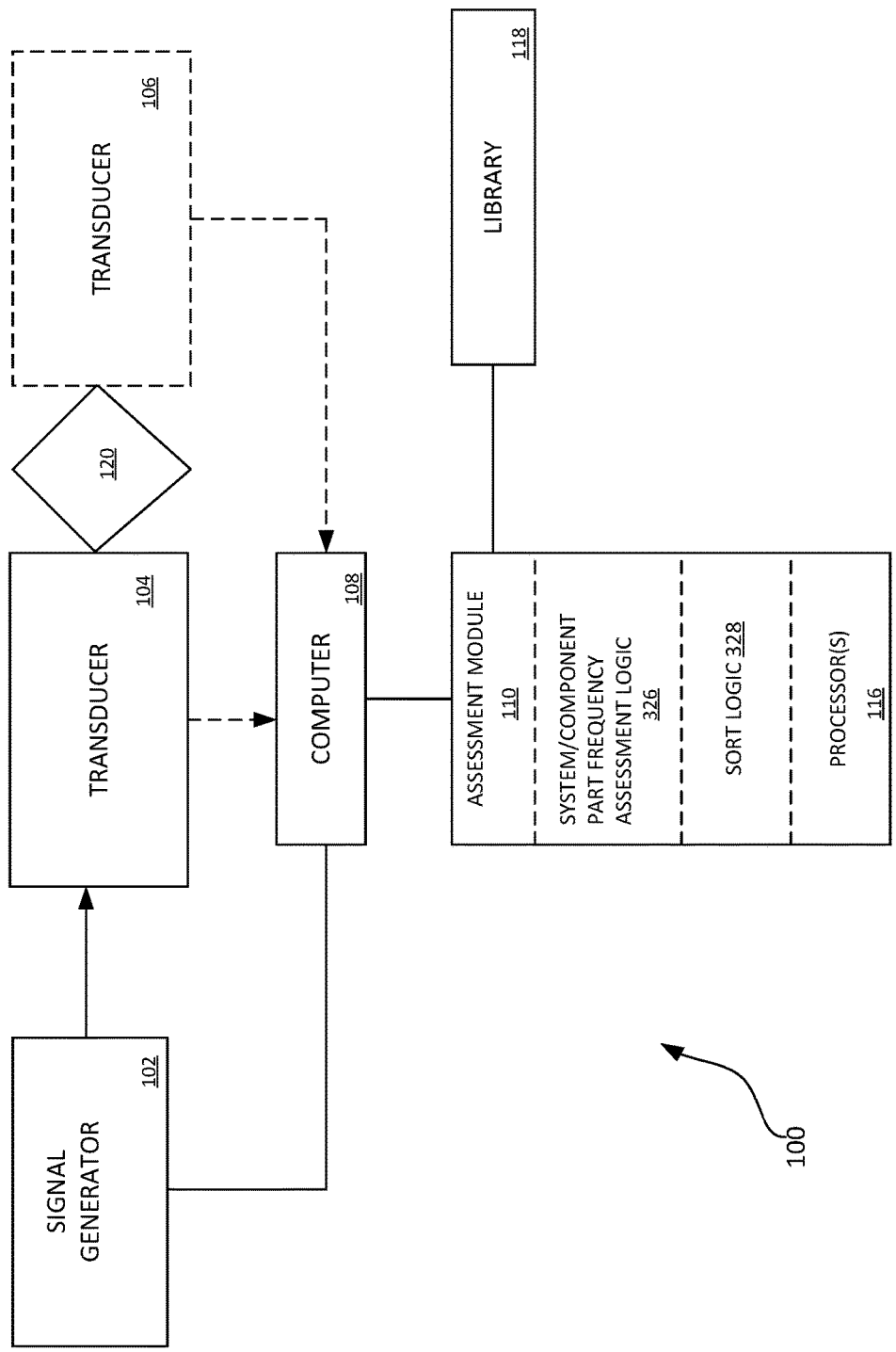
FIG. 12 is a block diagram of another embodiment of a resonance inspection tool that has an assessment module that is configured to provide a frequency assessment between a system and a component part of the system.

Another embodiment of a resonance inspection tool is illustrated in FIG. 12, is identified by reference numeral 100', and is a variation of the resonance inspection tool 100 discussed above. Unless otherwise noted, the discussion of the resonance inspection tool 100 is equally applicable to the resonance inspection tool 100', including without limitation with regard to the acquisition of data on a part 120. However, the resonance inspection tool 100' of FIG. 12 does include a modified assessment module 110' (e.g., incorporated/embodied by a non-transitory computer-readable storage medium). Principally, this assessment module 110' includes system/component part frequency assessment logic 326. The assessment module 110' may also incorporate sort logic 328 to perform a resonance inspection on a part 120 (including having the sort logic 328 being configured in accordance with one or more of the protocols that were discussed in relation to the resonance inspection tool 100).

A number of additional protocols for classifying a part will now be addressed, each of which may be utilized by the assessment module 110' of the resonance inspection tool 100', and each of which may be incorporated/embodied by a non-transitory computer-readable storage medium (e.g., each such protocol may be of a non-transitory form). Unless a resonance inspection is required by a particular one of these protocols, the resonance inspection tool 100' if course need not be configured to perform a resonance inspection, and as such it may be more generally referred to as a part evaluation system or tool 100' in conjunction with each of these protocols.

Any appropriate system (e.g., gearbox, transmission, jet engine) may be assessed using the system/component part frequency assessment logic 326 of the resonance inspection tool 100'. Such a system may include one or more subsystems or assemblies, one or more component parts (e.g., a gear, turbine blade), or any combination thereof. In any case, one or more moving component parts may be used by this system, one or more stationary parts may be used by this system, or both. A given component part of this type of system may move in any appropriate manner during at least part of the operation of the system at one or more steady-state operational frequencies (e.g., rotation, reciprocation, pivotal motion, translation). A "steady-state operational frequency" means where operation of the system is occurring on at least a substantially a constant basis (e.g., at a constant velocity; under non-accelerating conditions).

Figure 13:
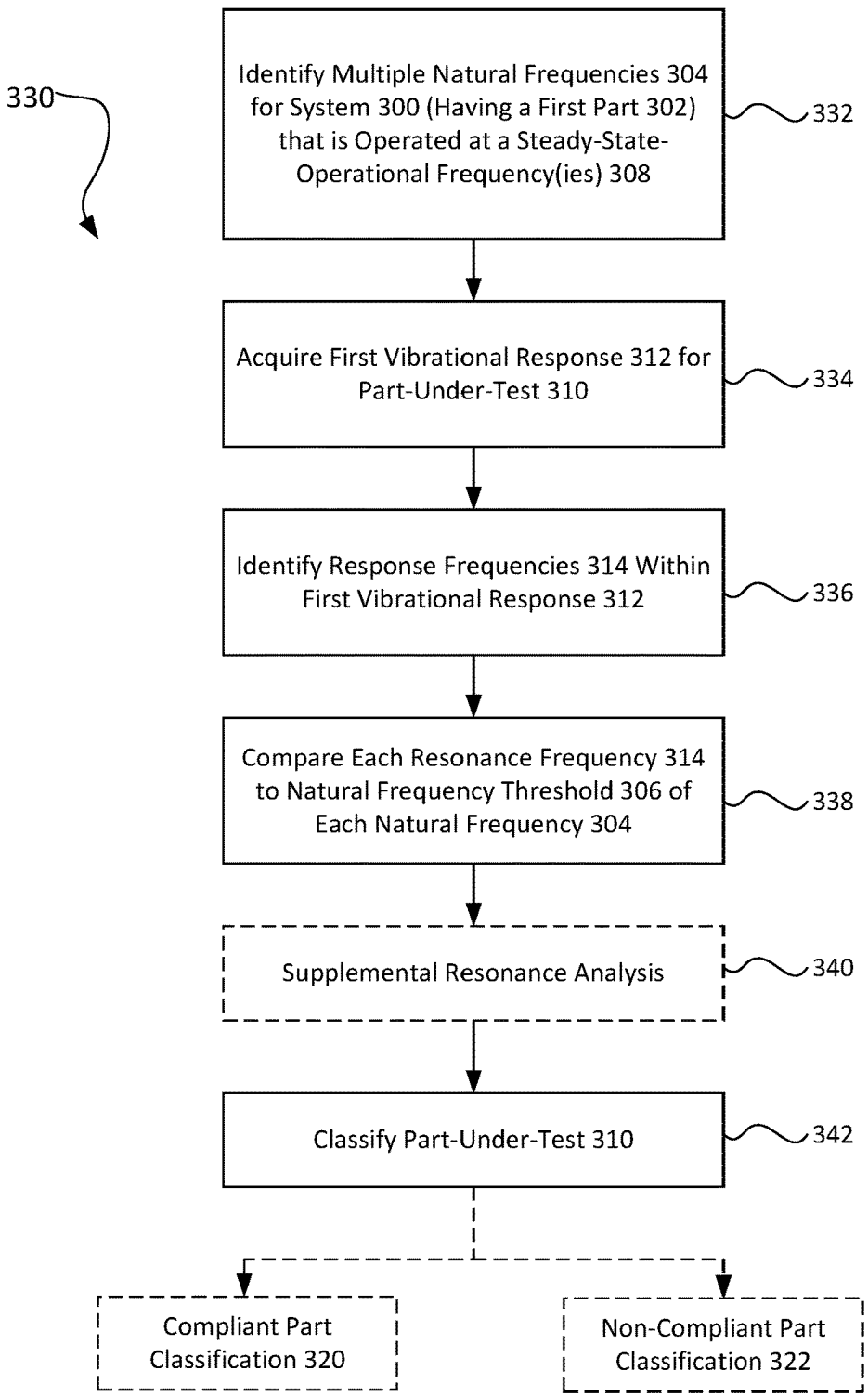
FIG. 13 is one embodiment of a part evaluation protocol.

One embodiment of a part evaluation protocol is illustrated in FIG. 13, is identified by reference numeral 330, and may be utilized by the system/component part frequency assessment logic 326 for the resonance inspection tool 100'. The part evaluation protocol 330 includes identifying a plurality of natural frequencies 304 for a system 300 that is operating at one or more steady-state operational frequencies 308 (step 332). The system 300 could be operated at a single steady-state operational frequency 308, or could be operated at any appropriate number of different steady-state operational frequencies 308. Any appropriate number of natural frequencies 304 may be identified pursuant to step 332 of the part evaluation protocol 330 (e.g., two or more) and that occur at one or more steady-state operational frequencies 308. The "natural frequency" in accordance with step 332 may be a natural frequency of the entirety of the system 300, may be a natural frequency of at least one sub-system or assembly of the system 300, may be the natural frequency of a particular component part of the system 300, or any combination thereof.

Natural frequencies 304 of the system 300 may be may be acquired in any appropriate manner for purposes of step 332 of the part evaluation protocol 332 of FIG. 13. Operation of the system 300 at one or more steady-state operational frequencies may be modeled (e.g., on a computer), and the natural frequencies 304 of the system 304 for step 332 of the protocol 330 may be acquired from this modeling (including in accordance with the modeling protocol 390 discussed below in relation to FIG. 18). Another option is to use functional testing of the system 300 to acquire the natural frequencies 304 of the system 300 for purposes of step 332 of the part evaluation protocol 300. "Functional testing" includes actual operation of the system 300 (or at least a prototype of the system 300). Computer modeling and functional testing may be used in combination to acquire the natural frequencies 304 of the system 300 for purposes of step 332 of the part evaluation protocol 300.

The part evaluation protocol 330 further requires the acquisition of a first vibrational response 312 for a part-under-test 310 (step 334). In this regard, the system 300 includes a first part 302, and the part-under-test 310 for purposes of the part evaluation protocol 300 may be used as the first part 302 for the system 300. This first part 302 may be stationary when installed and during operation of the system 300, may move continually in any appropriate manner when installed and during operation of the system 300, or may move in any appropriate manner at least at some point in time (e.g., intermittently; periodically; randomly) when installed and during operation of the system 300. In any case, the first vibrational response 312 may be the frequency response of the part-under-test 310, and may be acquired by the resonance inspection tool 100' in the manner discussed above with regard to the resonance inspection tool 100 (e.g., where a resonance inspection of the part-undertest 310 is undertaken with the resonance inspection tool 100'). For instance, the first vibrational response 312 for the part-under-test 310 may be acquired by installing the part-under-test 310 within the resonance inspection tool 100' (e.g., at a time when the part-under-test 310 is not installed in the system 300, or stated another way at a time when the part-under-test 310 is disassociated from the system 300).

One or more resonance frequencies 314 are identified within the first vibrational response 312 pursuant to step 336 of the part evaluation protocol 330 of FIG. 13. Step 336 may be executed by the resonance inspection tool 100'. Any appropriate number of resonance frequencies 314 may be identified within the first vibrational response 312, including each resonance frequency 314 within the first vibrational response 312.

Each resonance frequency 314 within the first vibrational response 312 (part-under-test 310) may be compared to a natural frequency threshold 306 of each natural frequency 304 (system 300; step 332) pursuant to step 338 of the part evaluation protocol 330 of FIG. 13. This comparison may be undertaken by the resonance inspection tool 100'. One or more of the natural frequency thresholds 306 for step 338 may be the same, one or more of the natural frequency thresholds 306 for step 338 may be different, or any combination thereof (e.g., the natural frequency threshold 306 need not be the same for each natural frequency 304, although such could be the case).

The natural frequency threshold 306 for step 338 of the part evaluation protocol 330 of FIG. 13 may be of any appropriate magnitude. Each natural frequency threshold 306 may define a frequency range of any appropriate magnitude. Each natural frequency 304 may be disposed anywhere within its corresponding natural frequency threshold 306. Although a given natural frequency 304 could be disposed in the middle of its corresponding natural frequency threshold 306, such need not be the case.

The part-under-test 310 is classified (step 342) based at least in part on the comparison from step 338 discussed above (e.g., the classification for step 342 may be based upon both the comparison of step 338, and a supplemental resonance analysis that may be conducted pursuant to step 340 of the protocol 330 and that will be discussed in more detail below; the classification for purposes of step 342 may be based solely on the comparison of step 338). For purposes of the part evaluation protocol 330, the part-under-test 310 may be classified as either a compliant part (e.g., assigned a compliant part classification 320) or a non-compliant part (e.g., assigned a non-compliant part classification 322). Classification of the part-under-test 310 may be undertaken by the resonance inspection tool 100'.

In the event that the part evaluation protocol 330 is configured without step 340: 1) the protocol 330 may be configured such that the part-under-test 310 is assigned a compliant part classification 320 if each resonance frequency 314 (step 336) for the part-under-test 310 is outside of the natural frequency threshold 306 (step 338) of each natural frequency 304 for the system 300 (step 332); and 2) the protocol 330 may be configured such that the part-under-test 310 is assigned a non-compliant part classification 322 if at least one resonance frequency 314 (step 336) for the part-under-test 310 is within the natural frequency threshold 306 (step 338) of at least one natural frequency 304 of the system 300 (step 332).

The part evaluation protocol 330 of FIG. 13 may be used to assess parts of any kind, including without limitation original equipment (OEM) parts, parts manufacturer approval (PMA) parts, parts that are candidates for approval as a parts manufacturer (PMA) part, or any part that is not an OEM part. The part evaluation protocol 330 may be executed at any appropriate time in relation to a particular part-under-test 310, including where the part-under-test 310 is a new production part as addressed above, after the part-under-test 310 has been in use as the first part 302 for the system 300 (e.g., exposed to operation of the system 300), or both. One embodiment has a part being evaluated in accordance with the part evaluation protocol 330 prior to ever having been used in the system 300 (e.g., prior to the original/initial installation of the part (as the first part 302) in the system 300, and including where the part is a new production part), and thereafter being evaluated in accordance with the part evaluation protocol 330 one or more times after the part has been used in an operating system 300 (e.g., after the part has been exposed to operation of the system 300—where the part-under-test 310 would then be in the form of an in-service part). One embodiment has a part being evaluated in accordance with the part evaluation protocol 330 prior to each time that the part is installed in the system 300 as a first part 302, including prior to the first time that the part is installed in the system 300 as a first part 302, as well as prior to each time that this same part is re-installed in the system 300 as a first part 302 (for instance, after the part has been removed from the system 300 for any purpose, including for a resonance inspection, for repair, for refurbishment, or any combination thereof).

Figure 14:
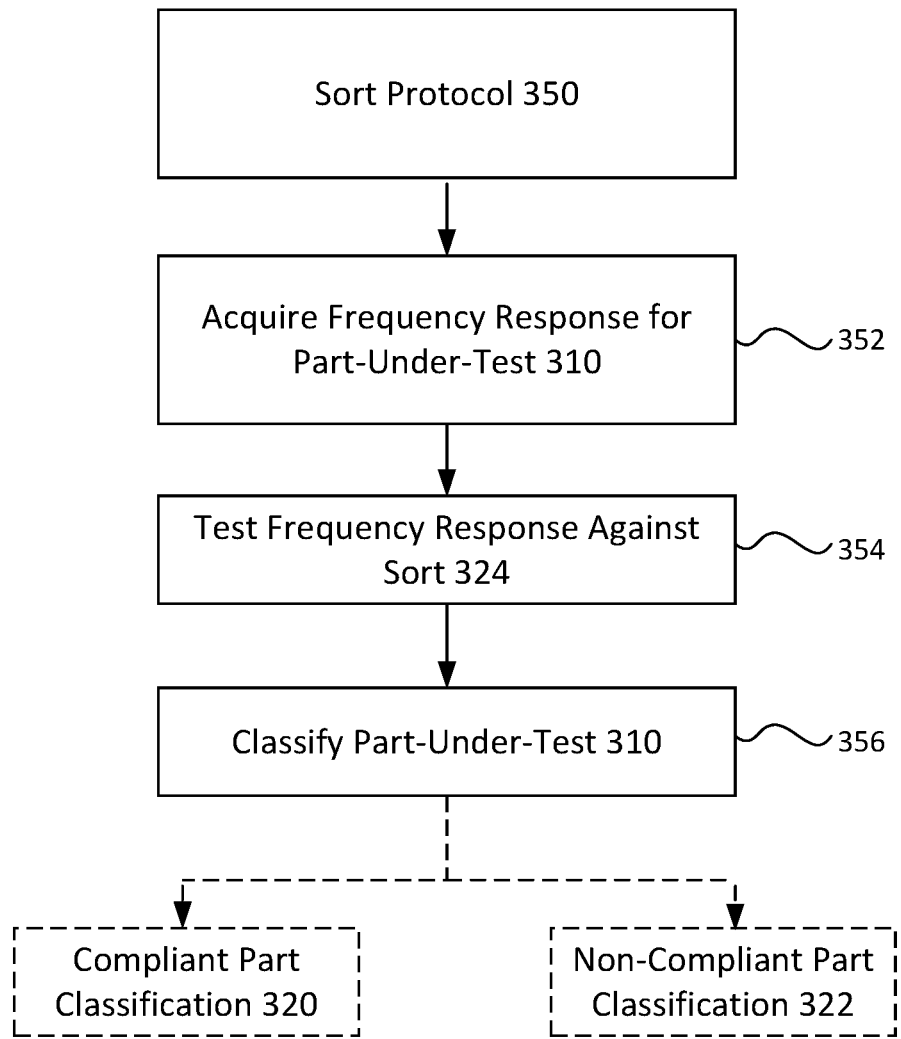
FIG. 14 is one embodiment of a sort protocol where a part-under-test is assessed in relation to a sort.

One embodiment of a sort protocol is presented in FIG. 14, is identified by reference numeral 350, may be used by step 340 of the part evaluation protocol 330 of FIG. 13, and may be utilized by the sort logic 328 for the resonance inspection tool 100' of FIG. 12. The sort protocol 350 can also be used independently of the part evaluation protocol 330. In any case, a frequency response is acquired for the part-under-test 310 pursuant to step 352. This frequency response may be acquired pursuant to execution of a resonance inspection of the part-under-test 310 in accordance with the foregoing. The frequency response for step 352 of the sort protocol 350 may be in the form of the first vibrational response 312 for the part evaluation protocol 330 of FIG. 13.

The frequency response (step 352) may be compared to or tested against a sort 324 through execution of step 354 of the sort protocol 350 of FIG. 14. The part-under-test 310 may be classified (step 356) based at least in part on this testing against the sort 324 (step 354). The part-under-test 310 may be assigned or designated a compliant part classification 320 or a non-compliant part classification 322 (step 356).

The frequency response (step 352) is tested against the sort 324 pursuant to step 354. A "sort 324", as used herein, is at least generally in accordance with the discussion of a resonance standard presented above. A sort 324 may be characterized as an algorithm or a combination of algorithms that are used to determine if at least one characteristic (e.g., an attribute and/or a relationship), and more typically to determine if a plurality of characteristics, exist in relation to a certain frequency response. For instance, a sort 324 may be configured to require a peak of at least a certain amplitude at one or more frequencies in a frequency response, the lack of any peak of at least a certain amplitude throughout one or more frequency ranges of a frequency response, a predetermined relationship between one or more peaks in a frequency response (e.g., an amplitude ratio threshold), and the like. In any case and if a given frequency response is characterized as passing a sort 324, this may mean that the corresponding part-under-test 310 includes the characteristic or combination of characteristics embodied or required by the sort 324. Conversely and if a given frequency response is characterized as failing a sort 324, this may mean that the corresponding part-under-test 310 fails to include one or more characteristics that are embodied or required by the sort 324. Alternatively: 1) the phrase "passing a sort" may be equated with the sort 324 providing a compliant part classification sort result; and 2) the phrase "failing a sort" may be equated with the sort 324 providing a non-compliant part classification sort result.

In the case where the sort protocol 350 of FIG. 14 is being used independently of the part evaluation protocol 330 of FIG. 13, the protocol 350 may be configured such that the part-under-test 310 is assigned a compliant part classification 320 (step 356) if: 1) the frequency response (step 352; e.g., the first vibrational response 312) passes the sort 324 (step 354) and where the sort 324 is configured to identify one or more predetermined characteristics of a compliant part; or 2) the frequency response (step 352; e.g., the first vibrational response 312) fails the sort 324 (step 354) and where the sort 324 is configured to identify one or more predetermined characteristics of a non-compliant part. In the case where the sort protocol 350 of FIG. 14 is being used independently of the part evaluation protocol 330 of FIG. 13, the protocol 350 may be configured such that the part-under-test 310 is assigned a non-compliant part classification 322 (step 356) if: 1) the frequency response (step 352; e.g., the first vibrational response 312) passes the sort 324 (step 354) and where the sort 324 is configured to identify one or more predetermined characteristics of a non-compliant part; or 2) the frequency response (step 352; e.g., the first vibrational response 312) fails the sort 324 (step 354) and where the sort 324 is configured to identify one or more predetermined characteristics of a compliant part.

As noted, the sort protocol 350 of FIG. 14 may be used by step 340 of the part evaluation protocol 330 of FIG. 13 (although the sort protocol 350 could itself be used to assess a part-under-test 310). In the case where the sort protocol 350 is used by step 340 of the part evaluation protocol 330, and pursuant to the classification step 342 of the part evaluation protocol 330, the protocol 330 may be configured such that the part-under-test 310 is assigned a compliant part classification 320 only if: 1) each resonance frequency 314 (step 336) for the part-under-test 310 is outside of the natural frequency threshold 306 (step 338) of each natural frequency 304 for the system 300 (step 332); and 2) the frequency response (step 352; e.g., the first vibrational response 312) passes the sort 324 (step 354) and where the sort 324 is configured to identify one or more predetermined characteristics of a compliant part (or where the frequency response fails the sort 324 and where the sort 324 is configured to identify one or more predetermined characteristics of a non-compliant part). In the case where the sort protocol 350 is used by step 340 of the part evaluation protocol 330, and pursuant to the classification step 342 of the part evaluation protocol 330, the protocol 330 may be configured such that the part-under-test 310 is assigned a non-compliant part classification 322 upon satisfaction of at least one of the following: 1) at least one resonance frequency 314 (step 336) for the part-under-test 310 is within the natural frequency threshold 306 (step 338) of at least one natural frequency 304 for the system 300 (step 332); and 2) the frequency response (step 352; e.g., the first vibrational response 312) passes the sort 324 (step 354) and where the sort 324 is configured to identify one or more predetermined characteristics of a non-compliant part (or where the frequency response fails the sort 324 and where the sort 324 is configured to identify one or more predetermined characteristics of a compliant part).

The sort 324 used by the sort protocol 350 of FIG. 14 may be based upon and/or developed from any appropriate data. For instance, the sort 324 may be based upon data acquired from the resonance inspection of one or more parts (including for the case where these parts were determined (on at least some basis) to be compliant (e.g., non-defective)). The sort 324 may be based upon a computer model of the first part 302. The sort 324 may be based upon functional testing of the first part 302 (or at least functional testing of a prototype of the first part 302). The sort 324 may be based upon data from two of more data sources, including any combination of the foregoing.

The sort protocol 350 of FIG. 14 may be used to assess any appropriate part-under-test 310, such as a new production part (e.g., one that has not yet been installed in the system 300 as a first part 302) or an in-service part (e.g., one that has been installed in the system 300 as a first part 302, and where the system 300 as been operated such that the part has been exposed to operating conditions). In the case where the part-under-test 310 is an in-service part, the sort protocol 350 may be configured to determine if the part is aging normally or abnormally, and including in accordance with the foregoing.

Figure 15:
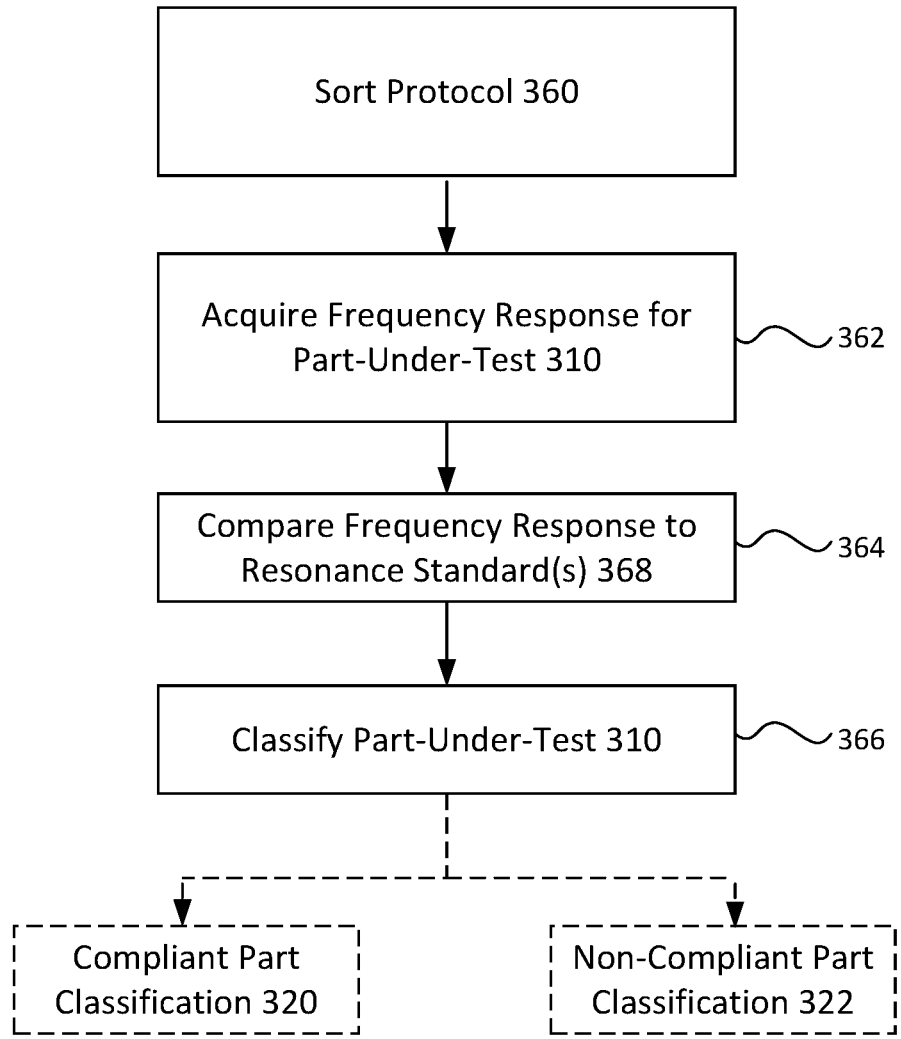
FIG. 15 is one embodiment of a sort protocol where a part-under-test is assessed against at least one resonance standard.

Another embodiment of a sort protocol is presented in FIG. 15, is identified by reference numeral 360, may be used by step 340 of the part evaluation protocol 330 of FIG. 13, and may be utilized by the sort logic 328 for the resonance inspection tool 100' of FIG. 12. The sort protocol 360 can also be used independently of the part evaluation protocol 330. In any case, a frequency response is acquired for the part-under-test 310 pursuant to step 362. This frequency response may be acquired pursuant to execution of a resonance inspection on the part-under-test 310 in accordance with the foregoing. The frequency response for step 362 of the sort protocol 360 may be in the form of the first vibrational response 312 for the part evaluation protocol 330 of FIG. 13.

The frequency response (step 362) may be compared to at least one resonance standard 368 through execution of step 364 of the sort protocol 360 of FIG. 15. The part-under-test 310 may be classified (step 366) based at least in part on this comparison (step 364). The part-under-test 310 may be assigned a compliant part classification 320 or a non-compliant part classification 322 (step 366).

The resonance standard 368 for purposes of step 364 of the sort protocol 360 of FIG. 15 may be in accordance with the foregoing. There could be one or more resonance standards 368 for parts that are assigned a compliant part classification 320 (e.g., an accepted part; a non-defective part), there could be one or more resonance standards 368 for parts that are assigned a non-compliant part classification 322 (e.g., a rejected part; a defective part), or both for purposes of step 364 of the sort protocol 360 of FIG. 15.

In the case where the sort protocol 360 of FIG. 15 is being used independently of the part evaluation protocol 330 of FIG. 13, the protocol 360 may be configured such that the part-under-test 310 is assigned a compliant part classification 320 (step 366) if: 1) the frequency response (step 352; e.g., the first vibrational response 312) complies with at least one resonance standard 368 that is used by the protocol 360 and that is associated with a compliant part (step 364); and/or 2) if the frequency response (step 352; e.g., the first vibrational response 312) does not comply with any resonance standard 368 that is used by the protocol 360 and that is associated with a non-compliant part. In the case where the sort protocol 360 of FIG. 15 is being used independently of the part evaluation protocol 330 of FIG. 13, the protocol 350 may be configured such that the part-under-test 310 is assigned a non-compliant part classification 322 (step 366) if: 1) the frequency response (step 352; e.g., the first vibrational response 312) complies with at least one resonance standard 368 that is used by the protocol 360 and that is associated with a non-compliant part (step 364); and/or 2) if the frequency response (step 352; e.g., the first vibrational response 312) fails to comply with at least one resonance standard 368 that is used by the protocol 360 and that is associated with a compliant part (step 364).

As noted, the sort protocol 360 of FIG. 15 may be used by step 340 of the part evaluation protocol 330 of FIG. 13 (although the sort protocol 360 could itself be used to assess a part-under-test 310). In the case where the sort protocol 360 is used by step 340 of the part evaluation protocol 330, and pursuant to the classification step 342 of the part evaluation protocol 330, the protocol 330 may be configured such that the part-under-test 310 is assigned a compliant part classification 320 only if: 1) each resonance frequency 314 (step 336) for the part-under-test 310 is outside of the natural frequency threshold 306 (step 338) of each natural frequency 304 for the system 300 (step 332); and 2) the frequency response (step 352; e.g., the first vibrational response 312) complies with at least one resonance standard 368 that is used by the protocol 360 and that is associated with a compliant part (step 364) (and/or where the frequency response does not comply with any resonance standard 368 that is used by the protocol 360 and that is associated with a non-compliant part). In the case where the sort protocol 360 is used by step 340 of the part evaluation protocol 330, and pursuant to the classification step 342 of the part evaluation protocol 330, the protocol 330 may be configured such that the part-under-test 310 is assigned a non-compliant part classification 322 upon satisfaction of at least one of the following: 1) at least one resonance frequency 314 (step 336) for the part-under-test 310 is within the natural frequency threshold 306 (step 338) of at least one natural frequency 304 for the system 300 (step 332); and 2) the frequency response (step 352; e.g., the first vibrational response 312) complies with at least one resonance standard 368 that is used by the protocol 360 and that is associated with a non-compliant part (step 364) (and/or where the frequency response fails to comply with at least one resonance standard 368 that is used by the protocol 360 and that is associated with a compliant part (step 364)).

The resonance standard(s) 368 used by the sort protocol 360 of FIG. 15 may be based upon and/or developed from any appropriate data. For instance, each resonance standard 368 may be based upon data acquired from the resonance inspection of one or more parts, including for the case where these parts were determined (on at least some basis) to be compliant (e.g., non-defective) or to be non-compliant (e.g., defective). Each resonance standard 368 may be based upon a computer model of the first part 302. Each resonance standard 368 may be based upon functional testing of the first part 302 (or at least functional testing of a prototype of the first part 302). Each resonance standard 368 may be based upon data from two of more data sources, including any combination of the foregoing.

The sort protocol 360 of FIG. 15 may be used to assess any appropriate part-under-test 310, such as a new production part (e.g., one that has not yet been installed in the system 300 as a first part 302) or an in-service part (e.g., one that has been installed in the system 300 as a first part 302, and where the system 300 as been operated such that the part has been exposed to operating conditions). In the case where the part-under-test 310 is an in-service part, the sort protocol 360 may be configured to determine if the part is aging normally or abnormally, and including in accordance with the foregoing.

Figure 16:
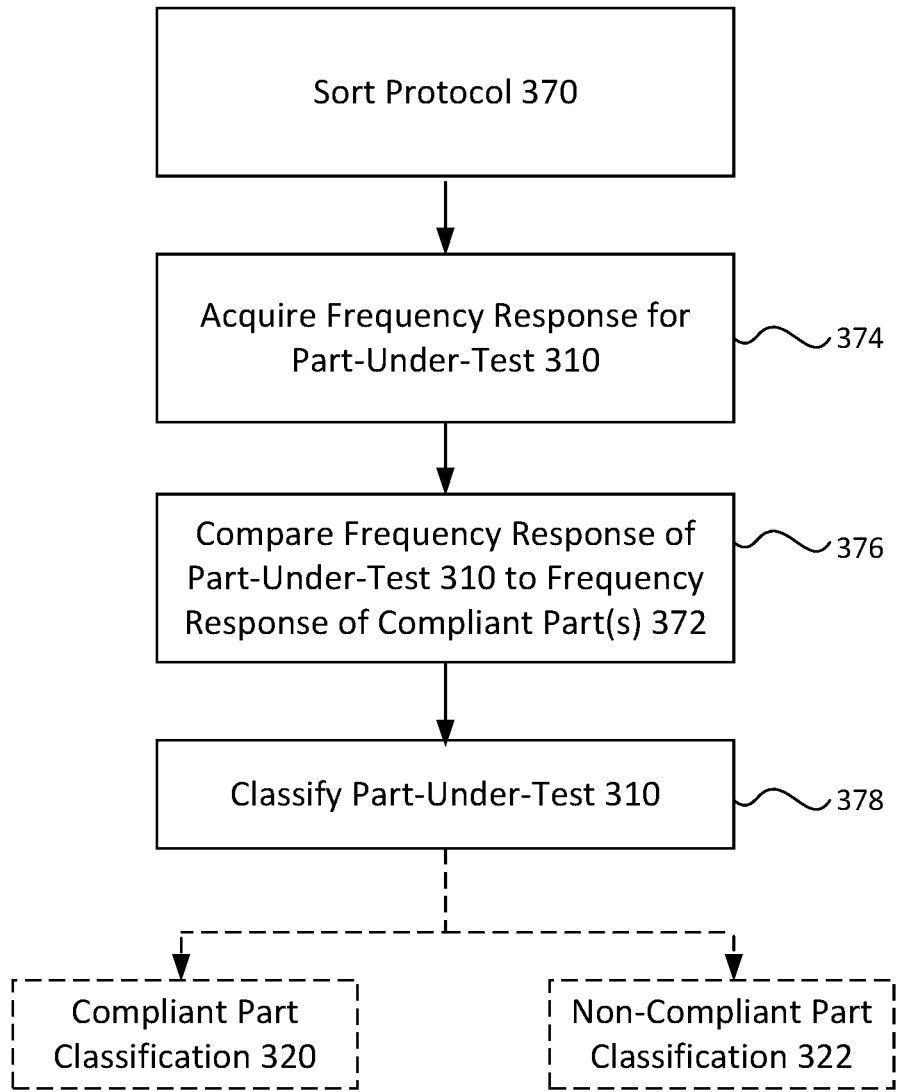
FIG. 16 is one embodiment of a sort protocol where a part-under-test is assessed by comparing its frequency response to the frequency response of at least one compliant part.

Another embodiment of a sort protocol is presented in FIG. 16, is identified by reference numeral 370, may be used by step 340 of the part evaluation protocol 330 of FIG. 13, and may be utilized by the sort logic 328 for the resonance inspection tool 100' of FIG. 12.

The sort protocol 370 can also be used independently of the part evaluation protocol 330. In any case, a frequency response is acquired for the part-under-test 310 pursuant to step 374. This frequency response may be acquired pursuant to execution of a resonance inspection of the part-under-test 310 in accordance with the foregoing. The frequency response for step 374 of the sort protocol 370 may be in the form of the first vibrational response 312 for the part evaluation protocol 330 of FIG. 13.

The frequency response (step 374) may be compared to the frequency response of one or more compliant parts through execution of step 376 of the sort protocol 370 of FIG. 16 (e.g., the frequency response of a compliant part may be in accordance with the resonance standard 368 discussed above in relation to the sort protocol 360 of FIG. 15). The frequency response of the part-under-test 310 and the frequency response of each compliant part used by the protocol 370 could be acquired through a resonance inspection in accordance with the foregoing (including where the part-under-test 310 and the compliant part(s) are exposed to the same drive frequencies or using the same frequency sweep). The part-under-test 310 may be classified (step 378) based at least in part on this comparison (step 376). The part-under-test 310 may be assigned a compliant part classification 320 or a non-compliant part classification 322.

As noted, the sort protocol 370 of FIG. 16 may be used by step 340 of the part evaluation protocol 330 of FIG. 13 (although the sort protocol 370 could itself be used to assess a part-under-test 310). In the case where the sort protocol 370 is used by step 340 of the part evaluation protocol 330, and pursuant to the classification step 342 of the part evaluation protocol 330, the protocol 330 may be configured such that the part-under-test 310 is assigned or designated a compliant part classification 320 only if: 1) each resonance frequency 314 (step 336) for the part-under-test 310 is outside of the natural frequency threshold 306 (step 338) of each natural frequency 304 for the system 300 (step 332); and 2) the frequency response (step 376; e.g., the first vibrational response 312) complies with the frequency response of at least one compliant part that is used by the protocol 370 (step 376). In the case where the sort protocol 360 is used by step 340 of the part evaluation protocol 330, and pursuant to the classification step 342 of the part evaluation protocol 330, the protocol 330 may be configured such that the part-under-test 310 is assigned a non-compliant part classification 322 upon satisfaction of at least one of the following: 1) at least one resonance frequency 314 (step 336) for the part-under-test 310 is within the natural frequency threshold 306 (step 338) of at least one natural frequency 304 for the system 300 (step 332); and 2) the frequency response (step 352; e.g., the first vibrational response 312) fails to comply with the frequency response of each compliant part that is used by the protocol 370 (step 376).

Figure 17:
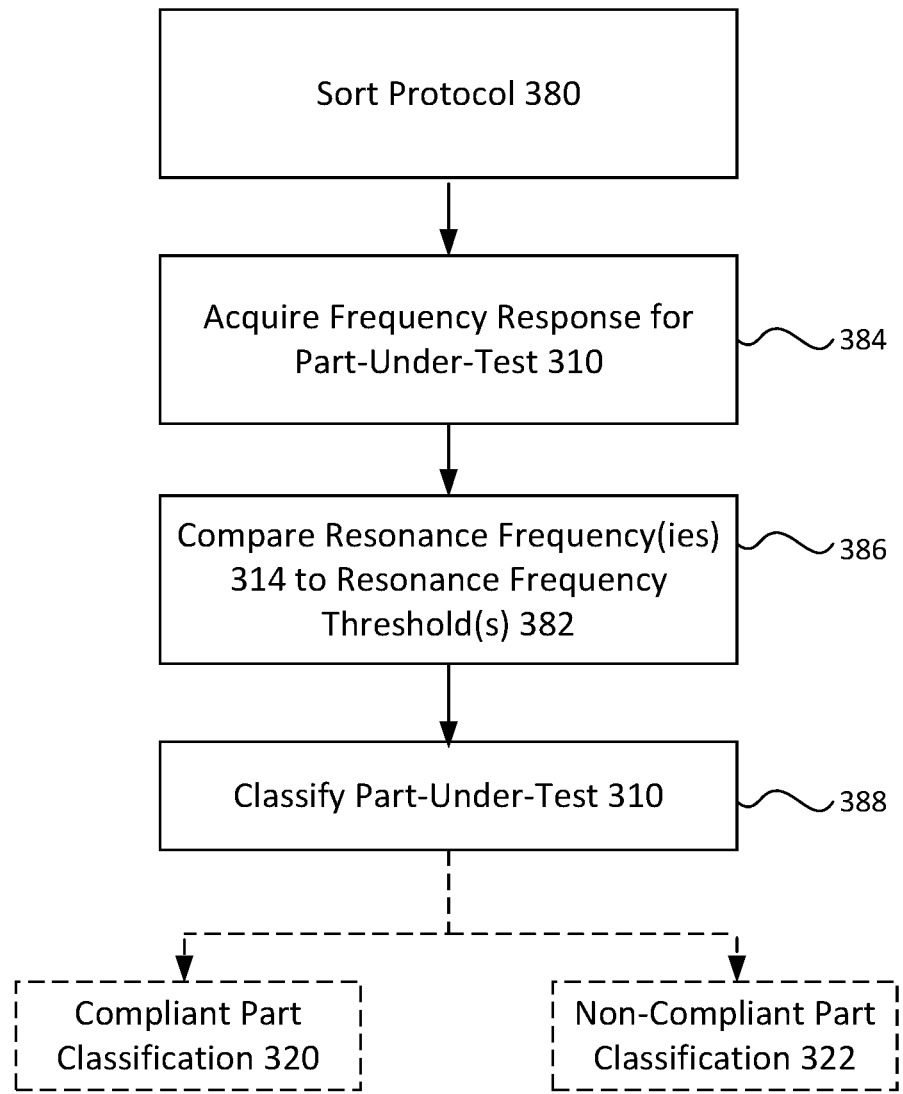
FIG. 17 is one embodiment of a sort protocol where a part-under-test is assessed by comparing one or more resonance frequencies of the part-under-test to one or more resonance frequency thresholds.

Another embodiment of a sort protocol is presented in FIG. 17, is identified by reference numeral 380, may be used by step 340 of the part evaluation protocol 330 of FIG. 13, and may be utilized by the sort logic 328 for the resonance inspection tool 100' of FIG. 12. A frequency response is acquired for the part-under-test 310 pursuant to step 384. This frequency response may be acquired pursuant to execution of a resonance inspection on the part-under-test 310 in accordance with the foregoing. The frequency response for step 384 of the sort protocol 380 may be in the form of the first vibrational response 312 for the part evaluation protocol 330 of FIG. 13.

The frequency response (step 384) may be compared to one or more resonance frequency thresholds 382 through execution of step 386 of the sort protocol 380 of FIG. 17. The resonance response of the part-under-test 310 may be acquired through a resonance inspection in accordance with the foregoing. In any case, the part-under-test 310 may be classified (step 388) based at least in part on this comparison (step 386). The part-under-test 310 may be assigned a compliant part classification 320 or a non-compliant part classification 322.

The protocol 380 may be configured such that one or more resonance frequencies 314 in the frequency response (step 384) are compared to one or more predetermined resonance frequency thresholds 382 (step 386). One or more predetermined resonance frequency thresholds 382 may be stored in the memory of the resonance inspection tool 100' for use by the protocol 380 (e.g., within the library 118). Each such resonance frequency threshold 382 may be defined in relation to a particular resonance frequency, and one or more predetermined characteristics of this particular resonance frequency (e.g., within +/–"x" of such a resonance frequency, with an amplitude of at least "y"). Each resonance frequency threshold 382 may be in the form of a certain frequency range, and furthermore may require a resonance frequency peak having an amplitude of at least a certain amount). That is, "complying" with a given resonance frequency threshold 382 means that there must be at least one resonance frequency 314 in the frequency response (step 384) that is within a frequency range associated with each resonance frequency threshold 382.

As noted, the sort protocol 380 of FIG. 17 may be used by step 340 of the part evaluation protocol 330 of FIG. 13 (although the sort protocol 380 could itself be used to assess a part-under-test 310, as will be discussed below). In the case where the sort protocol 380 is used by step 340 of the part evaluation protocol 330 (FIG. 13), and pursuant to the classification step 342 of the part evaluation protocol 330, the protocol 330 may be configured such that the part-under-test 310 is assigned or designated a compliant part classification 320 only if: 1) each resonance frequency 314 (step 336) for the part-under-test 310 is outside of the natural frequency threshold 306 (step 338) of each natural frequency 304 for the system 300 (step 332); and 2) a separate resonance frequency 314 for the part-under-test 310 complies with each resonance frequency threshold 382 that is used by the protocol 380 (step 386)—at least one resonance frequency 314 in the frequency response (step 384) exists within the frequency range associated with each resonance frequency threshold 382. In the case where the sort protocol 380 is used by step 340 of the part evaluation protocol 330 (FIG. 13), and pursuant to the classification step 342 of the part evaluation protocol 330, the protocol 330 may be configured such that the part-under-test 310 is assigned a non-compliant part classification 322 upon satisfaction of at least one of the following: 1) at least one resonance frequency 314 (step 336) for the part-under-test 310 is within the natural frequency threshold 306 (step 338) of at least one natural frequency 304 for the system 300 (step 332); and 2) a separate resonance frequency 314 for the part-under-test 310 fails to comply with each resonance frequency threshold 382 that is used by the protocol 380 (step 386)—at least one resonance frequency threshold 382 is not satisfied by any resonance frequency 314 in the frequency response (step 384) of the part-under-test 310.

The sort protocol 380 of FIG. 17 may also be used independently of the part evaluation protocol 330 of FIG. 13. The resonance frequency thresholds 382 for step 386 in this case may be based upon parts that have passed operational certification testing (an "operationally-certified part"). Initially, parts that are exposed to such operational certification testing are parts having a design that has not yet been approved for production/end-use (e.g., the part design (including both an original design and any subsequent re-design) has not yet been approved by one or more relevant entities or authorities; a part design (including both an original design and any subsequent re-design) lacks the appropriate certification or certifications from one or more relevant entities or authorities). "Operational certification testing" as used herein means actual testing of a part in its end use configuration (e.g., the part being incorporated into a device, assembly, or system, where this device, assembly, or system is then operated in accordance with one or more standards that are at least based upon the end-use application(s)). "Operational certification testing", as used herein, thereby encompasses "engine certification testing"—a process by which an engine manufacturer tests an engine (including all of its associated parts) and submits test data and other information (e.g., computations) on this engine to obtain a required certification from the relevant authority (e.g., the Federal Aviation Administration or FAA). "Operational certification testing" also thereby encompasses testing associated with obtaining Parts Manufacturer Approval—a process by which a third party replacement part is tested for use in another's engine, and where the third party submits test data and other information (e.g., computations) on this replacement part to obtain a required certification from the relevant authority (e.g., the FAA).

After operational certification testing of a given part has occurred (an operationally-tested part): 1) one or more a resonance inspections of this same operationally-tested part may be performed (e.g., in accordance with the resonance inspection protocol 130 of FIG. 5), and the results of each such resonance inspection (e.g., the frequency response of the operationally-tested part) are retained; and 2) the same operationally-tested part is subjected to non-destructive testing, destructive testing, or both to determine if the operationally-tested part passed the operational certification testing. Obviously the resonance inspection(s) of the operationally-tested part must be done prior to any destructive testing of the operationally-tested part. There also may be circumstances where it may be desirable to perform the resonance inspection of the operationally-tested part prior to subjecting this part to non-destructive testing.

An operationally-certified resonance standard 383 (FIG. 17A) for use by the sort protocol 380 of FIG. 17 may be defined from the frequency response of one or more parts that have each passed the requisite operational certification testing (an operationally-certified part). Preferably the operationally-certified resonance standard 383 is defined from multiple operationally-certified parts, although it could be based upon a single operationally-certified part. In any case, this operationally-certified resonance standard 383 may be based upon resonance testing of a part that has completed operational certification testing (and is determined to have passed this operational certification testing), but prior to any further use of this very same part (e.g., the resonance testing may be done on a "new" operationally-certified part). The operationally-certified resonance standard 383 in this case may be characterized as being for assessing new production parts—a new production part resonance standard 383. The operationally-certified resonance standard 383 could also be based upon resonance testing of an operationally-certified part, but where this resonance testing occurs after the part has been in service for some amount of time after having completed and passed operational certification testing (e.g., the resonance testing may be done on an "in-service" operationally-certified part). The operationally-certified resonance standard 383 in this case may be characterized as being for assessing in-service parts—an in-service resonance standard 383. It should be appreciated that the same operationally-certified part could be used to define plurality of different resonance standards 383 which may collectively define at least part of the life cycle for the part (e.g., each resonance standard 383 being associated with a different time in the life cycle of the part).

Figure 17A:
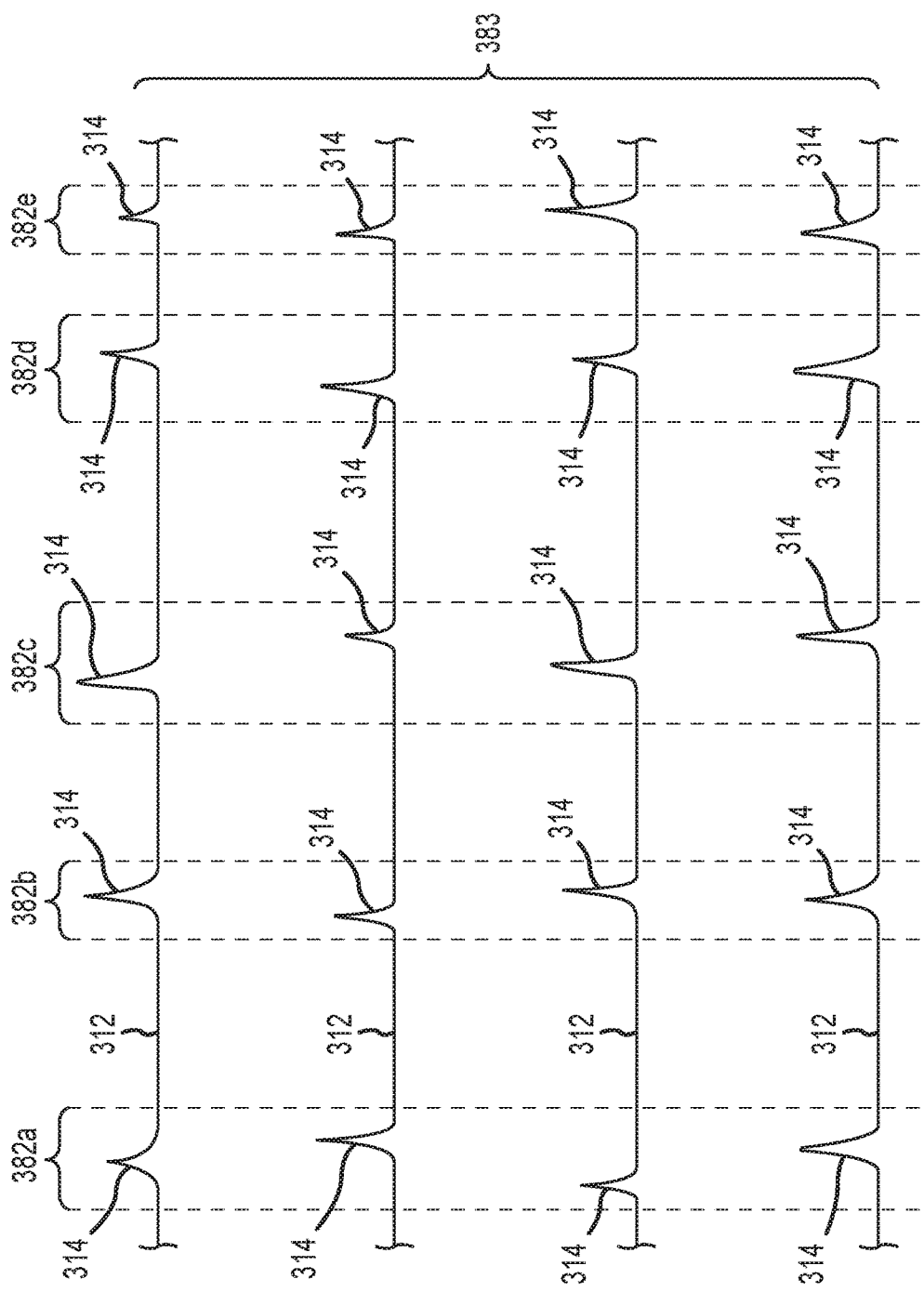
FIG. 17A is one embodiment of at least part of an operationally-certified resonance standard that may be defined by the frequency response of one or more operationally-certified parts, and that may be used by the sort protocol of FIG. 17.

In any case and referring to FIG. 17A, an operationally-certified resonance standard 383 may include one or more resonance frequency thresholds 382 as defined above. The operationally-certified resonance standard 383 of FIG. 17A is defined from four operationally-certified parts, where FIG. 17A presents the first vibrational or frequency response 312 for each such part. Any appropriate number of resonance frequency thresholds 382 may be used by an operationally-certified resonance standard 383 (five resonance frequency thresholds 382a-382e being illustrated in FIG. 17A). Generally, a resonance frequency 314 of the first vibrational or frequency response 312 of each operationally-certified part may be grouped with a resonance frequency 314 of the other vibrational or frequency responses 312 to define a corresponding resonance frequency threshold 382. Again, each resonance frequency threshold 382 may encompass a certain frequency range, and may require a resonance frequency 314 or resonance frequency peak of at least a certain amplitude within the corresponding frequency range.

An operationally-certified resonance standard 383 (FIG. 17A) may be used by the sort protocol 380 of FIG. 17, more specifically by step 386 of the sort protocol 380. The frequency response of the part-under-test 310 (step 384) may be compared to the operationally-certified resonance standard 383. If the part-under-test 310 complies with the operationally-certified resonance standard 383 (if the frequency response of the part-under-test 310 has a separate resonance frequency 314 that complies with each resonance frequency threshold 382 of the resonance standard 383 (e.g., where at least one resonance frequency 314 exists within the frequency range associated with each resonance frequency threshold 382)), the part-under-test 310 may be assigned to a compliant part classification 320 (step 388). If the part-under-test 310 fails to comply with the operationally-certified resonance standard 383 (e.g., if the frequency response of the part-under-test 310 does not have a resonance frequency 314 that complies with at least one of the resonance frequency thresholds 382 of the standard 383—a resonance frequency 314 does not exist within the frequency range associated with at least one of the frequency thresholds 382), the part-under-test 310 may be assigned to a non-compliant part classification 322 (step 388).

Modeling may be used in relation to one or more aspects of the part evaluation protocol 330 of FIG. 13 and as noted above. Modeling may be used to identify the natural frequencies 304 for the system 300 for purposes of step 332 of the part evaluation protocol 330. The frequency response of the part-under-test 310 (step 334) may be compared to a computer model of the first part 302 for purposes of step 340 of the part evaluation protocol 330, for instance where the sort 324 for step 354 of the sort protocol 350 (FIG. 14) is based at least in part on a computer model of the first part 302, or where one or more resonance standards 368 for step 364 of the sort protocol 360 (FIG. 15) are based at least in part on a computer model of the first part 302.

Figure 18:
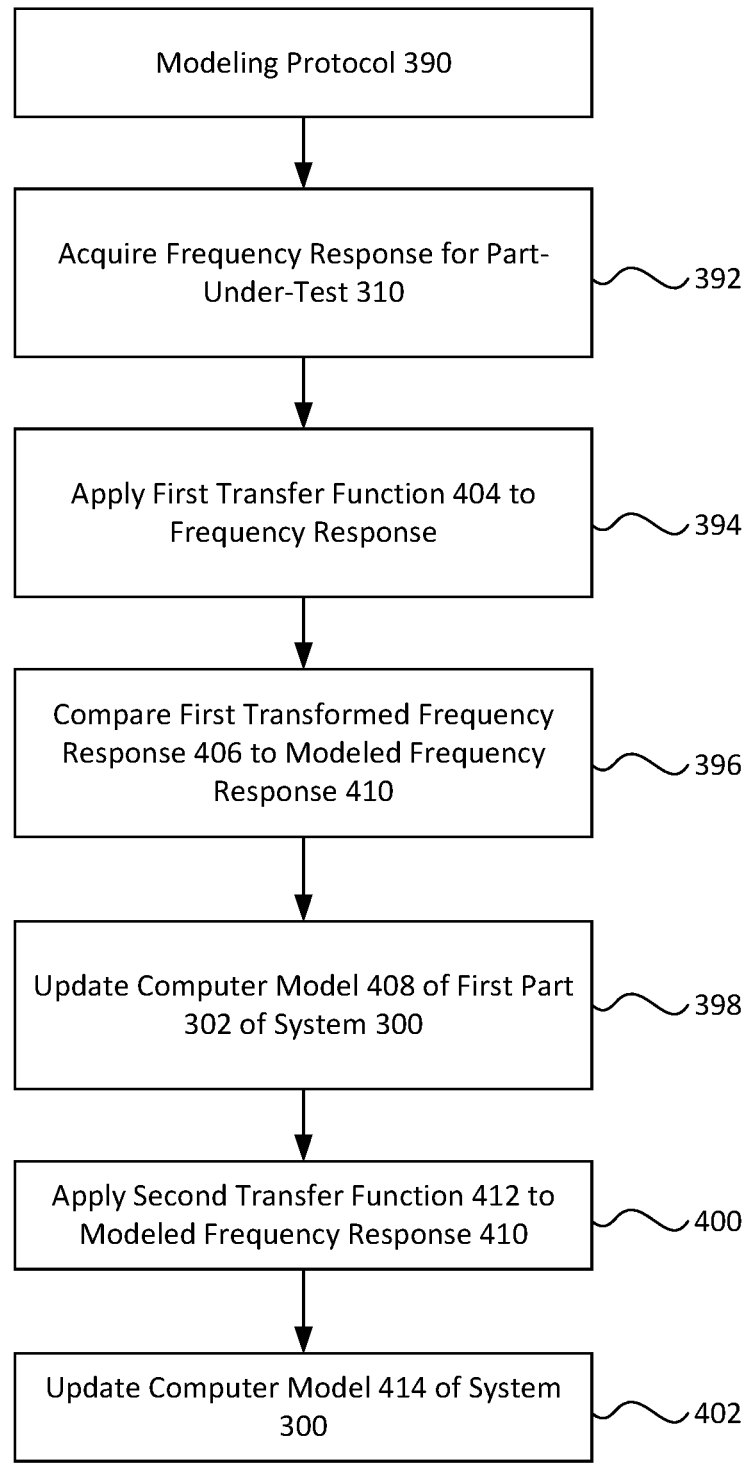
FIG. 18 is one embodiment of a modeling protocol.

One embodiment of a modeling protocol is presented in FIG. 18, is identified by reference numeral 390, may be stored on a non-transitory computer-readable storage medium, and may be executed by an appropriate computer. A frequency response is acquired for the part-under-test 310 pursuant to step 392. This frequency response may be acquired pursuant to execution of a resonance inspection on the part-under-test 310 in accordance with the foregoing, or otherwise in the same manner as has been described herein with regard to conducting a resonance inspection. The frequency response for step 392 of the modeling protocol 390 may be in the form of the first vibrational response 312 for the part evaluation protocol 330 of FIG. 13.

A first transfer function 404 is applied to the frequency response (step 392) pursuant to execution of step 394 of the modeling protocol 390. This first transfer function 404 defines the vibrational response of the part-under-test 310 (step 392) in free space, and which also may be referred to as a first transformed frequency response 406. The first transformed frequency response 406 (step 396) may be characterized as a transformation or translation of the frequency response (step 392) for when the part-under-test 310 is in free space. That is and in the case of the resonance inspection tool 100' of FIG. 12, the part-under-test 310 is contacted by the resonance inspection tool 100' (e.g., by one or more transducers 104, 106). This contact between the resonance inspection tool 100' and the part-under-test 310 will affect the frequency response of the part-under-test 310. The first transfer function 404 of step 394 may be characterized as predicting what the vibrational response of the part-under-test 310 would be if the resonance inspection tool 100' did not have to contact the part-under-test 310 for purposes of a resonance inspection.

Step 396 of the modeling protocol 390 is directed to comparing the above-noted first transformed frequency response 406 to a modeled frequency response 410. A "modeled frequency response 410" for purposes of step 396 of the modeling protocol 390 is a frequency response of the first part 302 of the system 300 that is predicted by a computer model 408 of the first part 302. Again and as noted above, the part-under-test 310 may be used as a first part 302 within the system 300. The computer model 408 for the first part 302 may be defined in any appropriate manner and may be used for any appropriate purpose, including for predicting the frequency response of the first part 302.

The computer model 408 of the first part 302 for the system 300 may be updated pursuant to the execution of step 398 of the modeling protocol 390 of FIG. 18, for instance based upon the first transformed frequency response 406. That is, data on the actual frequency response of the part-under-test 310 (after the application of the first transfer function 404) may be used to adjust the computer model 408 of the first part 302 for the system 300 (e.g., so that the computer model 408 of the first part 302 more closely approximates the part-under-test 310 at least on a vibrational response or frequency response basis). In any case, a second transfer function 412 may then be applied to the modeled frequency response 410 for the computer model 408 of the first part 302 (after any update of this computer model 408 pursuant to step 398) pursuant to execution of step 400 of the modeling protocol 390.

The second transfer function 412 associated with step 400 of the modeling protocol 390 predicts the frequency response of the first part 302 when installed within an operational system 300 (e.g., where the first part 302 may be contacted by one or more other parts of the system 300), including where the system 300 is operated in accordance with at least one steady-state operational frequency 308 (e.g., for purposes of step 332 of the part evaluation protocol 330 of FIG. 13). Updating of the computer model 408 for the first part 302 of the system 300 (step 398) may be viewed as updating a computer model 414 of the overall system 300—step 400 of the modeling protocol 390 may be used to update the computer model 414 of the overall system 300.

The updated computer model 414 of the system 300 (step 402 of the modeling protocol 390 of FIG. 18) may be used to identify one or more natural frequencies 304 of the system 300 for purposes of step 332 of the part evaluation protocol 330 of FIG. 13 (and furthermore may then be used to set each natural frequency threshold 306 that may be used by the part evaluation protocol 330). The updated computer model 408 of the first part 302 (step 398 of the modeling protocol 390 of FIG. 18) may be used for any appropriate purpose. The updated computer model 408 of the first part 302 (step 398 of the modeling protocol 390) could also be used as a data source for: 1) the sort 324 for the sort protocol 350 of FIG. 14 (including when used by step 340 of the part evaluation protocol 330 of FIG. 13), and/or 2) a resonance standard 368 for the sort protocol 360 of FIG. 15 (including when used by step 340 of the part evaluation protocol 330 of FIG. 13). The updated computer model 408 of the first part 302 could also be used in establishing the resonance frequency thresholds 382 for the sort protocol 380 of FIG. 17, for the case where the sort protocol 380 is used by step 340 of the part evaluation protocol 330 of FIG. 13.

The part evaluation protocol 330 of FIG. 13 (including the sort protocol 350 of FIG. 14; the sort protocol 360 of FIG. 15; the sort protocol 370 of FIG. 16; the sort protocol 380 of FIG. 17) may be used in any appropriate manner and for any appropriate purpose. A part that has been used as a first part 302 in the system 300 may be repaired and/or refurbished at one or more times. Such a repaired and/or refurbished part may be assessed through execution of the part evaluation protocol 330 and/or one or more of the sort protocols 350, 360, 370, and/or 380 (including at a time when the part has been removed from the system 300).

A redesign of a part may be assessed through execution of the part evaluation protocol 330 and/or one or more of the sort protocols 350, 360, 370, and/or 380. Consider the case where: 1) a first part-under-test 310 is in accordance with a first design; and 2) a different second part-under-test 310 is in accordance with a second design. In one embodiment, the first and second designs are each in accordance with a common product specifications standard, and each of the first and second parts-under-test 310 in this example may be assessed through execution of the part evaluation protocol 330 and/or one or more of the sort protocols 350, 360, 370, and/or 380. In another embodiment, the first design is in accordance with a first product specifications standard, the second design is in accordance with a second product specifications standard (which includes one or more updates of the first products specifications standard), and each of the first and second parts-under-test 310 in this example may be assessed through execution of the part evaluation protocol 330 and/or one or more of the sort protocols 350, 360, 370, and/or 380.

One or more aspects of manufacturing may be assessed through execution of the part evaluation protocol 330 and/or one or more of the sort protocols 350, 360, 370, and/or 380. Manufacturing specifications may apply to the first part 302 for the system 300. Consider the case where: 1) a first part-under-test 310 is manufactured in accordance with a first manufacturing protocol that is within a manufacturing specifications standard; and 2) a different second part-under-test 310 is some time thereafter manufactured in accordance with a second manufacturing protocol that is also within this same manufacturing specifications standard (e.g., the second manufacturing protocol may be an update of the first manufacturing protocol). In this case, each of the first and second parts-under-test 310 may be assessed through execution of the part evaluation protocol 330 and/or one or more of the sort protocols 350, 360, 370, and/or 380. The part evaluation protocol 330 and/or one or more of the sort protocols 350, 360, 370, and/or 380 may each then be characterized as evaluating changes in a manufacturing protocol, but where the "original" manufacturing protocol and the "updated" manufacturing protocol are each still in accordance with a predetermine manufacturing specifications standard.

Updated manufacturing specifications may be assessed through execution of the part evaluation protocol 330 and/or one or more of the sort protocols 350, 360, 370, and/or 380. Consider the case where: 1) a first part-under-test 310 is manufactured in accordance with a first manufacturing specifications standard; and 2) a different second part-under-test 310 is some time thereafter manufactured in accordance with a second manufacturing specifications standard (i.e., the second manufacturing specifications standard differs in at least one respect from the first manufacturing specifications standard). In this case, each of the first and second parts-under-test 310 may be assessed through execution of the part evaluation protocol 330 and/or one or more of the sort protocols 350, 360, 370, and/or 380. The part evaluation protocol 330 and/or one or more of the sort protocols 350, 360, 370, and/or 380 may each then be characterized as evaluating the "update" of the manufacturing specifications standard.

Each of the protocols 330, 350, 360, 370, and 380 may be used to assign a part-under-test 310 to a compliant part classification 320. Each of the protocols 330, 350, 360, 370, and 380 may be used to assign a part-under-test 310 to a non-compliant part classification 322. In the case of the sort protocols 350, 360, 370, and 380, the "compliant part classification 320" may be equated with an accepted part, with a non-defective part, or both. Conversely and for the sort protocols 350, 360, 370, and 380, the "non-compliant part classification 322" may be equated with a rejected part, with a part having one or more defects, or both.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method of evaluating a part, comprising the steps of:
identifying a plurality of natural frequencies that are generated by operation of a system at a first steady-state operational frequency, wherein said system comprises a first part;
vibrating a part-under-test by sweeping through a range of frequencies using a first transducer;
acquiring a first vibrational response to the vibrating of the part-under-test using a second transducer, the same as or different than the first transducer;
first identifying a plurality of resonance frequencies of said part-under-test from said first vibrational response;
comparing said plurality of resonance frequencies from said part-under-test with said plurality of natural frequencies from said system; and
classifying said part-under-test based upon said comparing step.

2. The method of claim 1, further comprising:
modeling operation of said system at said first steady-state operational frequency, wherein said natural frequency identification step is based upon said modeling step, and wherein said modeling step comprises using a computer.

3. The method of claim 1, further comprising:
functionally testing said system, wherein said natural frequency identification step is based upon said functionally testing step, and wherein said functionally testing step is executed in relation to operation of a prototype of said system at said first steady-state operational frequency.

4. The method of claim 1, wherein said plurality of natural frequencies for said natural frequency identification step is based upon both computer modeling operation of said system at said first steady-state operational frequency and functional testing of a prototype of said system operating at said first steady-state operational frequency.

5. The method of claim 1, wherein each natural frequency of said plurality of natural frequencies for said system has a separate natural frequency threshold, and wherein said classifying step comprises classifying said part-under-test as a compliant part if each resonance frequency of said plurality of resonance frequencies for said part-under-test is outside of said natural frequency threshold for each said natural frequency of said plurality of natural frequencies for said system.

6. The method of claim 1, wherein each natural frequency of said plurality of natural frequencies for said system has a separate natural frequency threshold, and wherein said classifying step comprises classifying said part-under-test as a non-compliant part if at least one resonance frequency of said plurality of resonance frequencies for said part-under-test is within said natural frequency threshold of at least one said natural frequency of said plurality of natural frequencies for said system.

7. The method of claim 1, further comprising:
acquiring a second vibrational response of said part-under-test using a third transducer, the same as or different than the first transducer and second transducer, wherein said acquiring a second vibrational response step is conducted after said part-under-test has been in service as said first part for said system;
second identifying a plurality of resonance frequencies of said part-under-test from said second vibrational response;
second comparing said plurality of resonance frequencies from said second identifying step with said plurality of natural frequencies from said system; and
second classifying said part-under-test based upon said second comparing step.

8. The method of claim 1, further comprising:
testing said first vibrational response against a sort, wherein said classifying step is further based upon said testing step.

9. The method of claim 8, wherein said classifying step comprises classifying said part-under-test as a compliant part only if: a) each resonance frequency of said plurality of resonance frequencies for said part-under-test is outside of said natural frequency threshold for each said natural frequency of said plurality of natural frequencies for said system; and b) said sort yields a sort result in the form of a compliant part classification.

10. The method of claim 8, wherein said classifying step comprises classifying said part-under-test as a non-compliant part based upon occurrence of at least one of the following: a) if at least one resonance frequency of said plurality of resonance frequencies for said part-under-test is within said natural frequency threshold of at least one said natural frequency of said plurality of natural frequencies for said system; and b) said sort yields a sort result in the form of a non-compliant part classification.

11. The method of claim 1, further comprising:
second comparing said first vibrational response to at least one resonance standard, wherein said classifying step is further based upon said second comparing step.

12. The method of claim 1, further comprising:
determining if said part-under-test resonates at least approximately the same as at least one compliant part, wherein said classifying step is further based upon said determining step.

13. The method of claim 1, further comprising executing said method for each of: 1) when said part-under-test is an original installation for said first part in said system; 2) each time said part-under-test is to be reinstalled in said system; and 3) and each time a new part-under-test is to be installed in said system as a replacement part.

14. The method of claim 1, wherein said part-under-test is selected from the group consisting of a new production part, an in-service part, an original equipment manufacturer (OEM) part, a parts manufacturer approval (PMA) part, and a candidate for approval as a parts manufacturer approval (PMA) part.

15. The method of claim 1, further comprising:
receiving said part-under-test from a manufacturer other than an original equipment manufacturer, wherein requirements for said classifying step are established by said original equipment manufacturer.

16. The method of claim 1, further comprising:
executing said method for a first said part-under-test, wherein said first said part-under-test is of a first design that is within a product specifications standard; and
executing said method for a second said part-under-test, wherein said second said part-under-test is a second design that is also within said product specifications standard but is different from said first design in a least one respect.

17. The method of claim 1, further comprising:
assessing a redesign of said first part of said system, wherein said assessing step comprises executing said method for said part-under-test in accordance with said redesign.

18. The method of claim 1, further comprising:
assessing a repair of said part-under-test after said part-under-test has been put into service with said system, wherein said assessing step comprising repeating said method for said part-under-test after having been repaired and prior to being reinstalled in said system.

19. The method of claim 1, further comprising:
executing said method for a first said part-under-test, wherein said first said part-under-test is manufactured according to a first manufacturing protocol that is within a manufacturing specifications standard; and
executing said method for a second said part-under-test, wherein said second said part-under-test is manufactured according to a second manufacturing protocol that is also within said manufacturing specifications standard but is different from said first manufacturing protocol in a least one respect.

20. The method of claim 1, further comprising:
assessing a manufacturing process modification for said first part of said system, wherein said assessing step comprises executing said method for said part-under-test resulting from said manufacturing process modification.

21. The method of claim 1, further comprising:
executing said method for a first said part-under-test, wherein said first said part-under-test is in accordance with a first product specifications standard for said first part in said system; and
executing said method for a second said part-under-test, wherein said second said part-under-test is in accordance with a second product specifications standard for the same said first part in said system, but where said second product specifications standard includes at least one update from said first product specifications standard.

22. The method of claim 1, further comprising:
second comparing each resonance frequency of said plurality of resonance frequencies from said part-under-test to a plurality of acceptable resonance frequency ranges for said first part.

23. The method of claim 1, further comprising:
second comparing said plurality of resonance frequencies of said part-under-test with resonance frequencies predicted by a computer model of said first part.

24. The method of claim 1, further comprising:
applying a first transfer function to said first vibrational response to define a second vibrational response for said part-under-test in free space;
comparing said second vibrational response to a computer model of said first part;
updating said computer model of said first part based upon said second vibrational response; and
applying a second transfer function to a predicted vibrational response from said computer model to define a third vibrational response for said first part in said system.

25. The method of claim 1, wherein said first vibrational response comprises a frequency response.

26. The method of claim 1, wherein said natural frequency identification step comprises identifying a plurality of natural frequencies that are generated by operation of a first system at said first steady-state operational frequency and at least one other different steady-state operational frequency.

27. The method of claim 1, wherein each natural frequency of said plurality of natural frequencies for said system has a separate natural frequency threshold, said method further comprising:
setting said natural frequency threshold.

* * * * *